US 8,623,041 B2

(12) United States Patent
Manabe

(10) Patent No.: US 8,623,041 B2
(45) Date of Patent: Jan. 7, 2014

(54) PUNCTURE TOOL, DEVICE FOR MEASURING BIOLOGICAL SAMPLE AND SYSTEM FOR MEASURING BIOLOGICAL SAMPLE

(75) Inventor: Kazuo Manabe, Ehime (JP)

(73) Assignee: Panasonic Corporation, Osaka (JP)

( * ) Notice: Subject to any disclaimer, the term of this patent is extended or adjusted under 35 U.S.C. 154(b) by 120 days.

(21) Appl. No.: 13/201,873

(22) PCT Filed: Feb. 18, 2010

(86) PCT No.: PCT/JP2010/001054
§ 371 (c)(1),
(2), (4) Date: Aug. 17, 2011

(87) PCT Pub. No.: WO2010/095442
PCT Pub. Date: Aug. 26, 2010

(65) Prior Publication Data
US 2011/0301629 A1 Dec. 8, 2011

(30) Foreign Application Priority Data

Feb. 18, 2009 (JP) ................................. 2009-034969

(51) Int. Cl.
A61B 17/32 (2006.01)
A61B 17/34 (2006.01)
(52) U.S. Cl.
USPC ........................................................ 606/182
(58) Field of Classification Search
USPC .......... 606/167, 170, 181, 182, 185; 600/309, 600/365, 573, 583; 455/26.1, 39, 455/41.1–41.3, 55.61; 340/539.12
See application file for complete search history.

(56) References Cited

U.S. PATENT DOCUMENTS

| 2004/0210247 | A1 | 10/2004 | Sonoda et al. | |
|---|---|---|---|---|
| 2008/0015623 | A1* | 1/2008 | Deck | 606/181 |
| 2008/0077048 | A1* | 3/2008 | Escutia et al. | 600/583 |
| 2009/0043253 | A1* | 2/2009 | Podaima | 604/67 |
| 2009/0143697 | A1* | 6/2009 | Tanaka | 600/565 |

FOREIGN PATENT DOCUMENTS

| JP | 2001-309905 | 11/2001 |
|---|---|---|
| JP | 2003-339680 | 12/2003 |

* cited by examiner

Primary Examiner — Ryan Severson
Assistant Examiner — Katherine M Shi
(74) Attorney, Agent, or Firm — Greenblum & Bernstein, P.L.C.

(57) ABSTRACT

Provided is a puncture tool having no possibility of starting the puncture operation of a puncture needle unexpectedly when the puncture tool is operated for a purpose other than measurement of a biological sample and also provided are a device for measuring biological sample and a system for measuring biological sample. A puncture tool (100) comprises a puncture mechanism (110), a puncture mechanism control section (120) which controls puncture operation of the puncture mechanism (110), a wireless communication section (140) which performs wireless authentication by receiving a wireless signal from an external registration apparatus (200), and a puncture control circuit (150) which removes restriction on puncture prohibition of the puncture mechanism control section (120) when authentication is established at the wireless communication section (140). The puncture tool (100) can perform operation for urging puncture only when a puncture permission signal is issued from an external registration apparatus (200) which is registered externally.

13 Claims, 14 Drawing Sheets

PUNCTURE TOOL, DEVICE FOR MEASURING BIOLOGICAL SAMPLE AND SYSTEM FOR MEASURING BIOLOGICAL SAMPLE

TECHNICAL FIELD

The present invention relates to a puncturing device, a biological sample measuring apparatus and a biological sample measuring system that do not start performing puncturing operation by mistake.

BACKGROUND ART

Patent literature 1 discloses a bodily fluid sampling device that can readily and reliably sample bodily fluid, with a simple configuration. A puncturing device described in Patent Literature 1 has a puncturing needle to puncture skin, a puncturing needle holding section that holds a puncturing needle and a biasing spring that applies biasing force to the puncturing needle holding section. In addition, the above-described puncturing device has a magnetic force retaining section that retains the puncturing holding portion in the base end side of the puncturing device by magnetic force, and a retention releasing section that has a solenoid to generate a magnetic field in a direction to offset the magnetic force of the magnetic force retaining section.

In order to perform puncturing, the user first compresses the biasing spring by drawing the puncturing needle holding section to the base end side of the puncturing device to lock the puncturing needle holding section in the magnetic force retaining section. Then, the user performs the operation including pressing a puncturing execution button, so that the retention releasing section applies a voltage to the solenoid to cancel the locked state. By this means, the puncturing needle projects from the tip of the puncturing device to puncture skin.

The above-described puncturing device has a configuration to electrically drive the retention releasing section. Therefore, a puncturing needle is released from being retained by the magnetic force retaining section by conducting electricity to the retention releasing section, so that it is possible to start the puncturing operation of the puncturing needle. In addition, the puncturing operation of a puncturing needle is started by energizing the retention releasing section, and therefore, when the puncturing execution button is pressed in a defective condition in which the retention releasing section does not completely and adequately apply a voltage to the solenoid, the puncturing operation of a puncturing needle is not started. In this way, this conventional puncturing device can prevent the puncturing operation of a puncturing needle from being started unexpectedly, in a condition in which electrical release requirements are not satisfied.

Citation List
Patent Literature
PTL 1
Japanese Patent Application Laid-Open No. 2003-339680

SUMMARY OF INVENTION

Technical Problem

However, even if the conventional puncturing device has a configuration to electrically perform releasing of the puncturing needle holding section from the locked state, it is not possible to prevent the puncturing operation of a puncturing needle from being started unexpectedly if electrical requirements for releasing are satisfied. For example, a case is possible where a child plays with this puncturing device, not only a case where biological samples are measured. Then, a case is possible where electrical release requirements are satisfied unexpectedly in process of playing with the puncturing device. Conventionally, there has been a problem that, when a puncturing device is operated for purposes other than measurement of biological samples, the puncturing operation of a puncturing needle is likely to be started unexpectedly.

It is therefore an object of the present invention to provide a puncturing device, a biological sample measuring apparatus and a biological sample measuring system that prevents a puncturing needle from unexpectedly starting puncturing operation when the puncturing device is operated for purposes other than measurement of biological samples.

Solution to Problem

The puncturing device according to the present invention adopts a configuration to include: a puncturing mechanism that actuates a puncturing needle; a puncturing mechanism control section that controls the puncturing mechanism to allow/disallow puncturing operation; a radio communication section that receives a radio signal from an external registration device; and a control section that releases the puncturing mechanism control section from restricting and disallowing puncturing when the radio communication section receives a predetermined radio signal.

The biological sample measuring apparatus according to the present invention that measures a biological sample obtained by puncturing by means of a puncturing device adopts a configuration to include: a biological sample measuring section that measures a biological sample; and a radio communication section that transmits a puncturing allowing signal that allows the puncturing device to perform puncturing, when the biological sample measuring section is ready to start measurement.

The biological sample measuring system according to the present invention including a puncturing device and a biological sample measuring apparatus that measures a biological sample obtained by puncturing by means of the puncturing device, wherein: the puncturing device includes: a puncturing mechanism that actuates a puncturing needle; a puncturing mechanism control section that controls the puncturing mechanism to allow/disallow puncturing operation; radio communication section that receives a radio signal from the biological sample measuring apparatus; and a control section that releases the puncturing mechanism control section from restricting and disallowing puncturing when the radio communication section receives a predetermined radio signal, and the biological sample measuring apparatus includes: a biological sample measuring section that measures a biological sample; and a radio communication section that transmits a puncturing allowing signal that allows the puncturing device to perform puncturing, when the biological sample measuring section is ready to start measurement.

Advantageous Effects of Invention

According to the present invention, it is possible to disallow the puncturing operation of a puncturing device unless a biological sample measuring apparatus resides nearby the puncturing device and is ready to perform measurement. Therefore, it is possible to realize a puncturing device, a measuring apparatus and a measuring system that prevents a puncturing needle from unexpectedly starting puncturing operation when the puncturing device is operated for purposes other than measurement of biological samples.

DESCRIPTION OF EMBODIMENTS

Now, embodiments of the present invention will be described in detail with reference to the accompanying drawings.

(Embodiment 1)

Figure 1A:
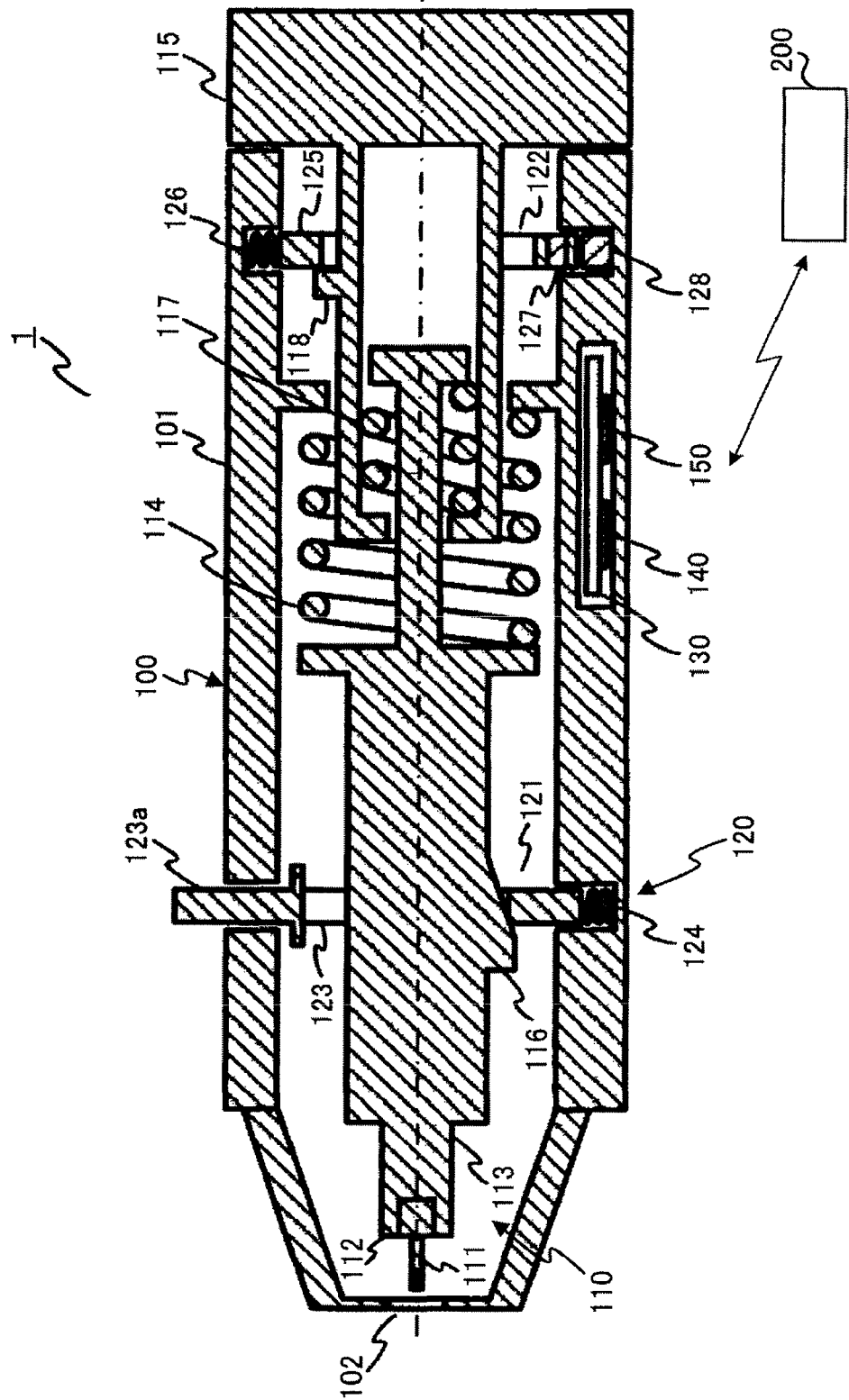
FIG. 1A is a cross sectional view showing a puncturing device according to Embodiment 1 of the present invention.
Figure 1B:
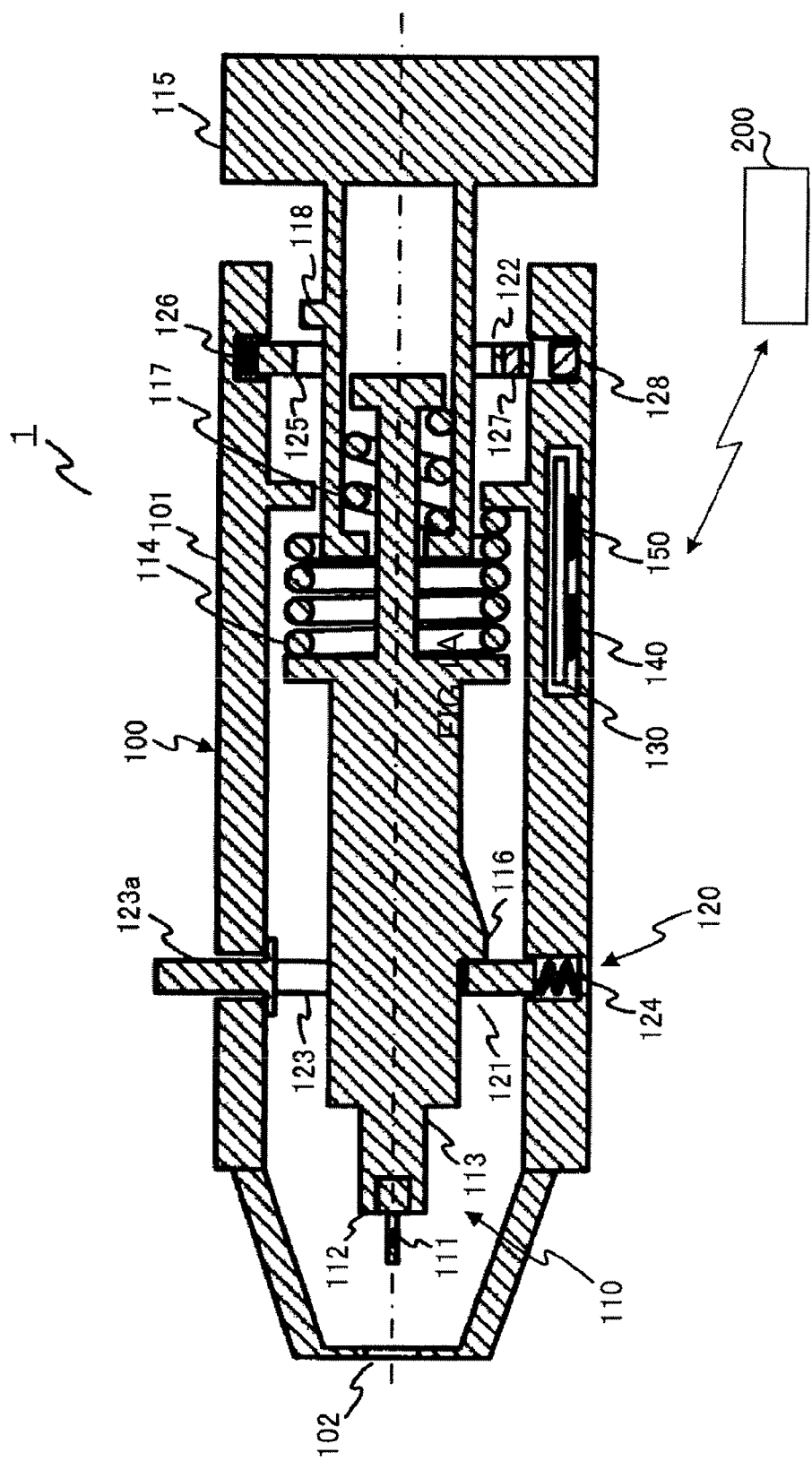
FIG. 1B is a cross sectional view showing the puncturing device according to Embodiment 1.

FIG. 1 is a cross sectional view showing a puncturing device according to Embodiment 1 of the present invention. FIG. 1A shows a state in which puncturing is disabled, and FIG. 1B shows a state in which puncturing is enabled and biasing force is applied. The present embodiment is an example in which the present invention is applied to a puncturing device having a puncturing needle to puncture skin, a puncturing needle holding section that holds the puncturing needle, and a biasing spring to apply biasing force to the puncturing needle holding section.

As shown in FIG. 1, biological sample measuring system 1 has puncturing device 100, and external registration device 200 that transmits puncturing allowing request signals to puncturing device 100.

Puncturing device 100 has casing 101, puncturing mechanism 110, puncturing mechanism control section 120 and substrate 130 which are arranged in casing 101, and radio communication section 140 and puncturing control circuit 150 which are placed on substrate 130. Casing 101 is a cylindrical housing and accommodates puncturing mechanism 110, puncturing mechanism control section 120 and substrate 130.

External registration device 200 transmits puncturing allowing request signals to puncturing device 100. For example, external registration device 200 is a biological sample measuring apparatus that has a biological sample measuring means for measuring biological samples and a radio communication means for transmitting a puncturing allowing request signal to puncturing device 100 when the biological sample measuring means is ready to perform measurement.

[Puncturing Mechanism 110]

Puncturing mechanism 110 has puncturing needle 111 to puncture skin and puncturing needle holding section 113 that holds puncturing needle 111 in tip part 112. In addition, puncturing mechanism 110 has biasing spring 114 that biases puncturing needle holding section 113 in the direction to project puncturing needle holding section 113 toward tip side 102 of puncturing device 100, and biasing operation section 115 that pulls puncturing needle holding section 113 to the rear end side (opposite to tip side 102) of puncturing device 100.

Locking convex part 116 that locks puncturing needle holding section 113 is provided on the side surface of puncturing needle holding section 113. The rear end side (opposite to tip part 112) of puncturing needle holding section 113 is connected to biasing operation section 115 via spring 117. As shown in FIG. 1B, the user pulls biasing operation section 115 to the rear end side of puncturing device 100 to compress biasing spring 114 and move puncturing needle holding section 113 to the biased position. Biasing operation section 115 is a knob part for pulling operation by the user against biasing spring 114.

Biasing control convex part 118 to limit movement of biasing operation section 115 to the rear end side of puncturing device 100, is provided on the side surface of biasing operation section 115.

[Puncturing Mechanism Control Section 120]

Puncturing mechanism control section 120 controls whether or not to enable puncturing mechanism 110 to perform puncturing. Puncturing mechanism control section 120 has locking mechanism 121, biasing control mechanism 122 and puncturing control circuit 150 placed on substrate 130.

Locking mechanism 121 is composed of locking ring 123 and locking ring spring 124.

Locking ring 123 is an annular component through which puncturing needle holding section 113 penetrates. Locking ring 123 abuts on locking convex part 116 provided on the side surface of puncturing needle holding section 113 when puncturing needle holding section 113 moves to the biased position. By this means, locking ring 123 locks puncturing needle holding section 113 in the biased position. In addition, as shown in FIG. 1, locking ring 123 is provided with puncturing trigger 123a projecting from casing 101 to the exterior in the position facing locking ring spring 124.

Locking ring spring 124 contacts the end of locking ring 123 opposite to puncturing trigger 123a to consistently apply force to make puncturing trigger 123a project from casing 101. The user presses puncturing trigger 123a to release puncturing needle holding section 113 from the locked state (perform puncturing). By this operation, locking ring spring 124 is compressed to release the contact state between locking ring 123 and locking convex part 116, and resultant biasing force makes puncturing mechanism 110 perform puncturing operation.

Biasing control mechanism 122 is formed by biasing control ring 125, biasing control ring spring 126, permanent magnet 127 and solenoid 128. Biasing control mechanism 122 switches whether or not to enable the user to apply biasing force to puncturing mechanism 110, based on a control signal outputted from puncturing control circuit 150.

Biasing control ring 125 is an annular component to which biasing operation section 115 penetrates. Permanent magnet 127 is embedded in one end of biasing control ring 125, and biasing control ring sprig 126 contacts the other end.

If the user pulls biasing operation section 115 to the rear end side (opposite to tip part 112) of puncturing device 100 when puncturing is not enabled (in a state in which the operation of biasing operation section 115 is disabled), biasing control ring spring 126 applies biasing force to biasing control ring 125. To be more specific, biasing control ring spring 126 applies biasing force to biasing control ring 125 to retain biasing control ring 125 in the position in which biasing control convex part 118 provided on the side surface of biasing operation section 115 interferes with biasing control ring 125.

Biasing control ring spring 126 is partly or entirely accommodated in a concave part of the inner wall of casing 101. As shown in FIG. 1B, when puncturing is enabled, biasing control ring spring 126 is compressed by basing control ring 125.

Solenoid 128 is embedded in the inner wall of casing 101 contacting one end side in which permanent magnet 127 in biasing control ring 125 is embedded. Repulsive force works between permanent magnet 127 and solenoid 128 due to a magnetic field generated by solenoid 128. When repulsive force works between permanent magnet 127 and solenoid 128, biasing control ring 125 is pressed on biasing control ring spring 126. This pressing force makes biasing control ring spring 126 be compressed, and biasing control ring 125 moves to the inner wall side of case 101 in which biasing control ring spring 126 is accommodated, as shown in FIG. 1B. As a result of this, interference between biasing control ring 125 and biasing control convex part 118 is cancelled.

By this means, the user can pull biasing operation section 115 to the rear end side, so that it is possible to lock puncturing needle holding section 113 in the biased position.

[Radio Communication Section 140]

Radio communication section 140 is formed by a communication module that performs bidirectional radio communication with a radio communication means in external registration device 200 using, for example, a weak radio frequency band of 300 MHz. The power consumption of this communication module is low.

Radio communication section 140 receives radio signals from external registration device 200 using a specific short-range radio communication scheme. Alternatively, radio communication section 140 receives radio signals from external registration device 200, using a low power short-range bidirectional radio communication scheme, such as Bluetooth (registered trademark) and UWB.

[Puncturing Control Circuit 150]

Puncturing control circuit 150 is electrically connected with solenoid 128 to control whether or not to make solenoid 128 generate a magnetic field. Puncturing control circuit 150 is mounted on substrate 130, together with radio communication section 140, and electrically connected with radio communication section 140.

Figure 2:
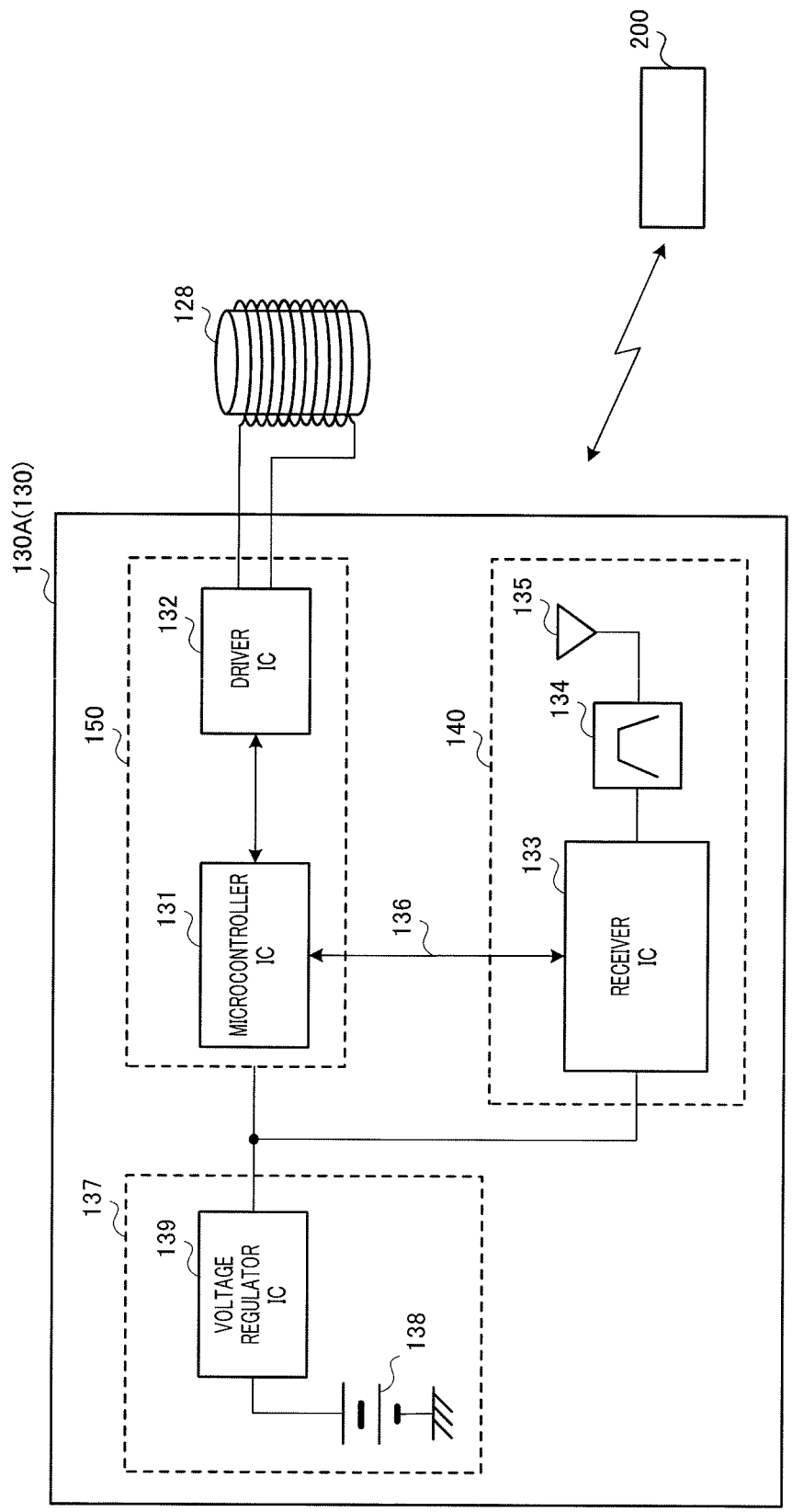
FIG. 2 is a block diagram showing an electrical circuit section in the puncturing device according to Embodiment 1.

FIG. 2 is a block diagram showing electrical circuit section 130A in puncturing device 100. Electrical circuit section 130A is formed on substrate 130.

As shown in FIG. 2, electrical circuit section 130A has microcontroller IC 131, driver IC 132, receiver IC 133, filter 134, antenna 135, serial communication means 136 and power supply circuit 137.

The above-mentioned receiver IC 133, filter 134 and antenna 135 constitute radio communication section 140.

The above microcontroller IC 131 and driver IC 132 constitute puncturing control circuit 150.

Upon receiving an interrupt request from radio communication section 140, microcontroller IC 131 reads data stored in radio communication section 140. Then, microcontroller IC 131 decides whether or not the serial number of the data stored in radio communication section 140 matches the serial number registered in a memory (not shown) provided in microcomputer IC 131. When the numbers match, microcontroller IC 131 decides whether or not the data stored in radio communication section 140 is a puncturing allowing signal, and, when it is a puncturing allowing signal, issues a driving request to driver IC 132. Here, issuing a driving request refers to outputting a control signal from microcontroller IC 131 to driver IC 132 to command solenoid 128 to drive via driver IC 132 (the same shall apply hereinafter). In addition, upon receiving, as input, a signal indicating that puncturing performed by puncturing mechanism 110 has been detected, from a puncturing detecting section (not shown), microcontroller IC 131 commands driver IC 132 to stop supplying a drive current.

To enable execution of puncturing operation, driver IC 132 supplies a drive current to solenoid 128, according to a command from microcontroller IC 131. When microcontroller IC 131 issues a driving request, driver IC 132 starts supplying a drive current to solenoid 128. This drive current generates a magnetic field in the direction in which solenoid 128 generates repulsive force against permanent magnetic 127.

Receiver IC 133 has a demodulation function and an error detection function, demodulates a signal received by antenna 135, and then performs error detection processing on a demodulated signal, and stores correctly received data in an embedded memory. Receiver IC 133 is connected to microcontroller IC 131 in puncturing control circuit 150 by serial communication means 136, and transmits and receives commands and data.

Filter 134 is inserted between receiver IC 133 and antenna 135 in order to reduce interference of out-of-band radio waves when antenna 135 receives signals.

Antenna 135 receives a radio signal transmitted from the outside of puncturing device 100, and outputs the received signal to receiver IC 133 via filter 134. Antenna 135 is a small chip antenna made of, for example, a high dielectric material.

Serial communication means 136 is, for example, a UART (universal asynchronous receiver transmitter) or a SPI (serial peripheral interface). Both a UART and a SPI are used with a general serial communication scheme.

Electrical circuit 137 is mounted on substrate 130 and supplies power to puncturing control circuit 150 and radio communication section 140. Power supply circuit 137 is composed of coin battery 138 and voltage regulator IC 139 to supply a constant voltage.

Now, the operation of puncturing device 100 configured as described above will be explained.

Figure 3:
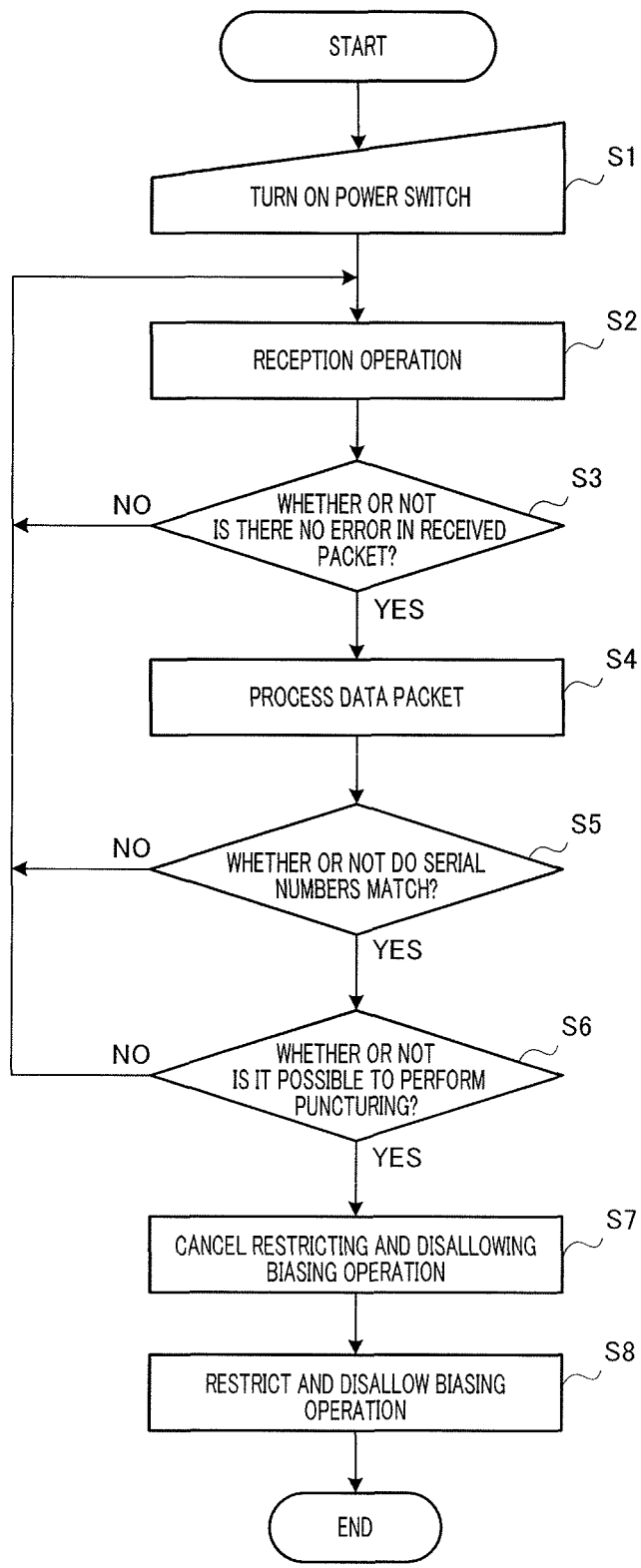
FIG. 3 is a flowchart showing processing steps from turn on of power to execution of puncturing regarding the puncturing device according to Embodiment 1.

FIG. 3 is a flowchart showing processing steps from turnon of power to execution of puncturing regarding puncturing device 100.

First, in step S1, when the user turns on a power switch (not shown), the step moves to step S2 to perform receiving operation.

In step S2, microcontroller IC 131 commands receiver IC 133 in radio communication section 140 to be placed in a receiving state via serial communication means 136.

In step S3, receiver IC 133 performs error detection on a received data packet, and, when there is no error, moves to step S4, and, on the other hand, when there is an error, returns to step S2 and continues the receiving operation.

In step S4, receiver IC 133 stores the data packet that has been decided that there is no error in step S3, in a memory embedded in receiver IC 133, and issues a signal reception interrupt to microcontroller IC 131 via serial communication means 136. Upon receiving a signal reception interrupt request from receiver IC 133, microcontroller IC 131 reads data stored in the embedded memory in receiver IC 133 via serial communication means 136.

In step S5, micro controller IC 131 identifies the serial number contained in the data packet. If this serial number matches the serial number registered in advance in the memory embedded in microcontroller IC 131, the step moves to the next step S6. On the other hand, if the serial numbers do not match, the step returns to step S2 and the receiving operation is continued. The above-described serial number is a number unique to puncturing device 100, and is contained in packet data to prevent puncturing operation from being allowed mistakenly by a puncturing allowing signal transmitted to different puncturing device 100.

In step S6, microcontroller IC 131 interprets the content of the data packet and decides whether or not it represents a puncturing allowing signal. If the content of the data packet indicates a puncturing allowing signal, the step moves to the next step S7. If the content represents information other than a puncturing allowing signal, the step returns to step S2 and the receiving operation is continued.

In step S7, microcontroller IC 131 cancels disallowing biasing operation. In the initial state, microcontroller IC 131 does not issue a solenoid driving request to driver IC 132, so that solenoid 128 and permanent magnet 127 do not interact with one another, and biasing control ring 125 and biasing control convex part 118 contact. During cancellation of disallowing biasing operation in step S7, microcontroller IC 131 issues a solenoid driving request to driver IC 132, and driver IC 132 supplies a drive current to solenoid 128. By this means, repulsive force works between solenoid 128 and permanent magnetic 127 to cancel interference between biasing control ring 125 and biasing control convex part 118 and releases biasing operation section 115 from the biasing operation disallowing state.

In step S8, the user presses puncturing trigger 123*a* after pulling and operating biasing operation section 115 to lock puncturing needle holding section 113 in a biased state. By pressing puncturing trigger 123*a*, locking ring 123 releases puncturing needle holding section 113 from the locked state in the biased position. By this means, puncturing mechanism 110 is released from the locked state. Meanwhile, microcontroller IC 131 receives, as in put, a detection signal from a puncturing detecting section (not shown). Microcontroller IC 131 knows that puncturing has been performed, by receiving the detection signal from puncturing detecting section. Microcontroller IC 131 outputs a control signal to driver IC 132. Driver IC 132 stops supplying a driving current to solenoid 128 and places biasing operation section 115 in the biasing operation disallowing state again. This biasing operation disallowing state is the above-described initial state in which biasing control ring 125 and biasing control convex part 118 contact.

As described above, according to the present embodiment, puncturing device 100 has puncturing mechanism 110, puncturing mechanism control section 120 that controls the puncturing operation of puncturing mechanism 110, radio communication section 140 that receives radio signals from external registration device 200 and performs radio authentication, and puncturing control circuit 150 that releases puncturing mechanism control section 120 from restricting and disallowing puncturing when radio communication section 140 provides authentication. Puncturing device 100 cannot perform biasing operation for puncturing unless external registration device 200 issues a puncturing allowing signal. For example, when external registration device 200 is a biological sample measuring apparatus, it is possible to disallow puncturing device 100 from performing puncturing operation unless the biological sample measuring apparatus (external registration device 200) resides nearby puncturing device 100. Therefore, it is possible to prevent puncturing device 100 from mistakenly performing puncturing when puncturing device 100 is operated for purposes other than measurement of biological samples.

That is, biological sample measuring system 1 is used with collaboration between a biological sample measuring apparatus (external registration device 200) and puncturing device 100. Puncturing device 100 cannot perform puncturing unless a biological sample measuring apparatus resides near puncturing device 100. On that condition, the biological sample measuring apparatus measures biological samples.

When a biological sample measuring apparatus outputs a puncturing allowing signal at the time to measure biological samples, it is possible to prevent a puncturing device from mistakenly performing puncturing for purposes other than measurement of biological samples.

(Embodiment 2)

Figure 4A:
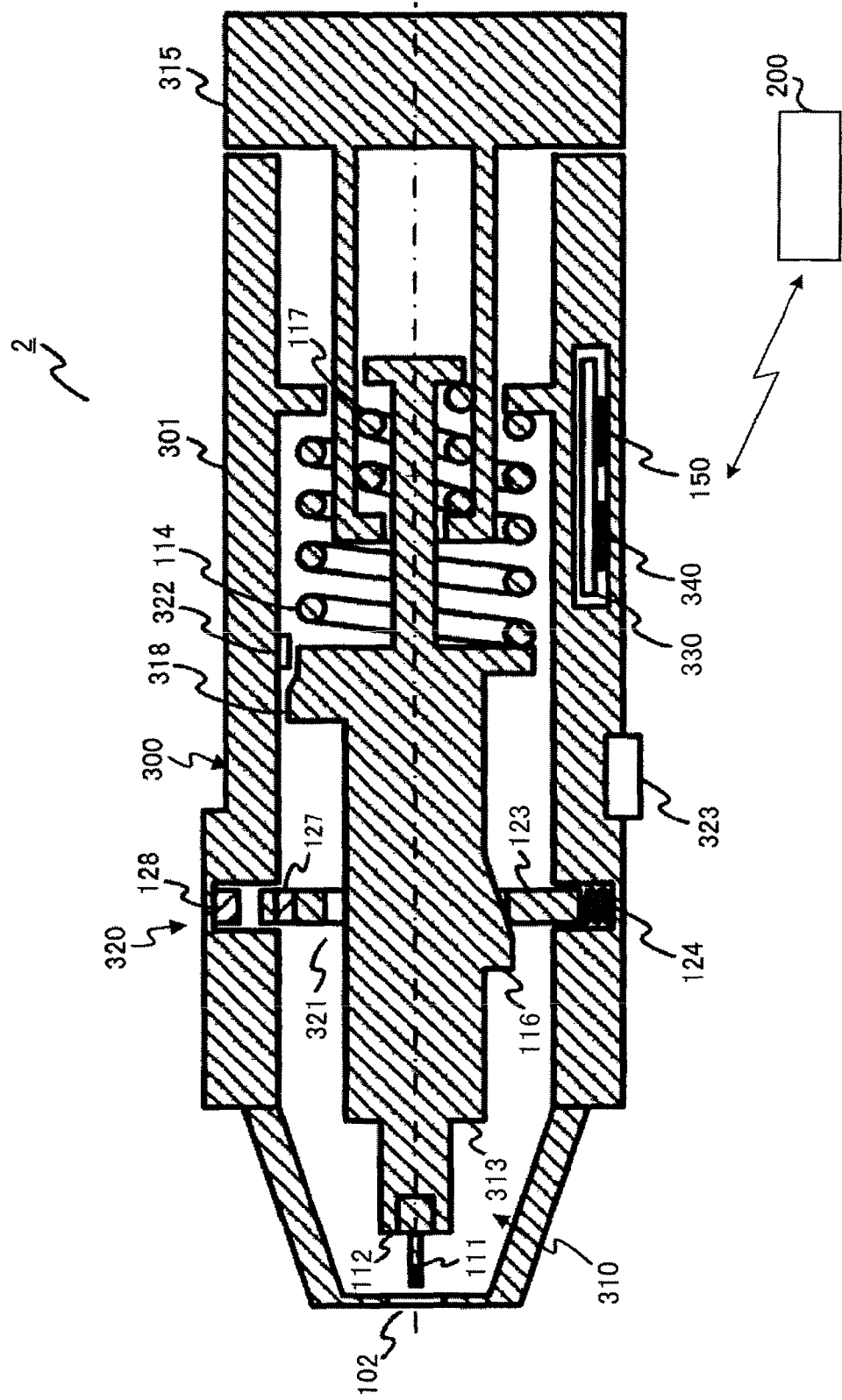
FIG. 4A is a cross sectional view showing a puncturing device according to Embodiment 2 of the present invention.
Figure 4B:
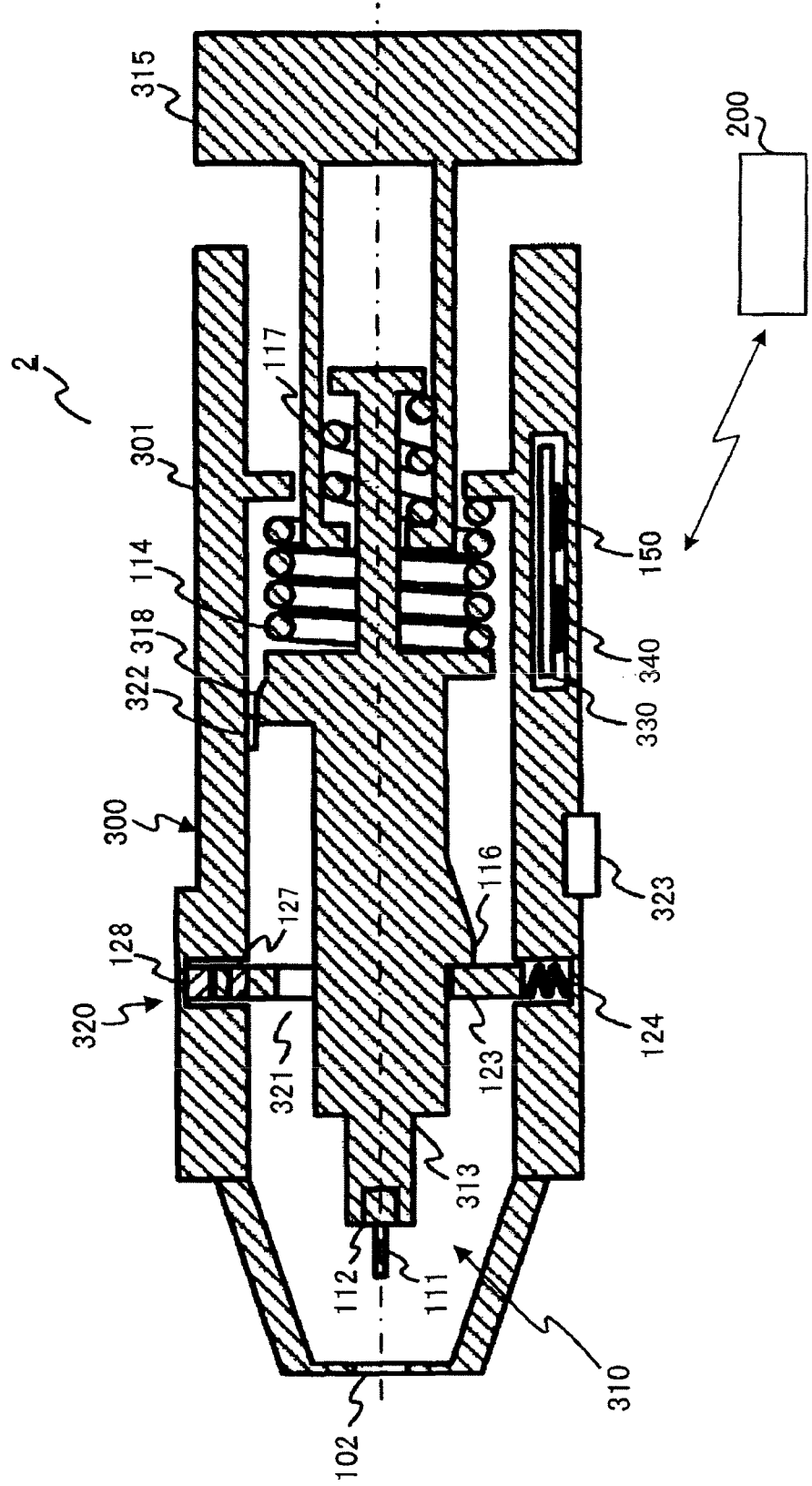
FIG. 4B is a cross sectional view of the puncturing device according to Embodiment 2.

FIG. 4 is a cross sectional view showing a puncturing device according to Embodiment 2 of the present invention. FIG. 4A shows a state in which puncturing is disabled, and FIG. 4B shows a state in which puncturing is enabled and biasing force is applied. To explain the present embodiment, the same components as in FIG. 1 are assigned the same reference numerals and overlapping descriptions will be omitted.

As shown in FIG. 4, biological sample measuring system 2 has puncturing device 300, and external registration device 200 that transmits puncturing allowing signals to puncturing device 300.

Puncturing device 300 has casing 301, puncturing mechanism 310, puncturing mechanism control section 320 and substrate 330 which are arranged in casing 301, and radio communication section 340 and puncturing control circuit 150 which are placed on substrate 330.

[Puncturing Mechanism 310]

Puncturing mechanism 310 has puncturing needle 111, puncturing needle holding section 313 that holds puncturing needle 111 in tip part 112, biasing spring 114 that biases puncturing needle holding section 313 in the direction to project puncturing needle holding section 313 toward tip side 102 of puncturing device 300, and biasing operation section 315 that pulls puncturing needle holding section 313 to the rear end side (opposite to tip side 102) of puncturing device 300.

Locking convex part 116 to lock puncturing needle holding section 313 and convex part 318 to press biasing detecting switch 322 are provided on the side surface of puncturing needle holding section 313.

The rear end side (opposite to tip part 112) of puncturing needle holding section 313 is connected to biasing operation section 315 via spring 117. As shown in FIG. 4B, the user pulls biasing operation section 315 to the rear end side of puncturing device 300 to compress biasing spring 114 and move puncturing needle holding section 313 to a biased position.

[Puncturing Mechanism Control Section 320]

Puncturing mechanism control section 320 controls whether or not to enable puncturing mechanism 310 to perform puncturing. Puncturing mechanism control section 320 has locking control mechanism 321, biasing detecting switch 322, puncturing control circuit 150 placed on substrate 330.

Locking control mechanism 321 is composed of locking ring 123, locking ring spring 124, permanent magnet 127, solenoid 128 and puncturing execution button 323.

Locking ring 123 is an annular component to penetrate puncturing needle holding section 313. When puncturing needle holding section 313 moves to a biased position, locking ring 123 abuts on locking convex part 116 provided on the side surface of puncturing needle holding section 313. By this means, locking ring 123 locks puncturing needle holding section 313 in a biased position. Holding ring spring 124 having the other end fixed to casing 301 contacts the locking convex part 116 side of locking ring 123.

Meanwhile, permanent magnet 127 is provided in the position facing locking ring spring 124 in locking ring 123. Locking ring spring 124 is a spring member to consistently apply force such that this permanent magnet 127 is pressed on solenoid 128 embedded in the inner wall of casing 301. Solenoid 128 generates repulsive force against permanent magnet 127. When repulsive force works between this permanent magnet 127 and solenoid 128, locking ring spring 124 is compressed, and locking ring 123 and locking convex part 116 do not contact to release puncturing needle holding section 313 from the locked state. Puncturing needle holding section 313 moves to tip side 102 of puncturing device 300 and puncturing needle 111 projects from tip side 102 of puncturing device 300 to perform puncturing.

Puncturing execution button 323 is a switch to be pressed by the user to perform puncturing. Puncturing execution button 323 is electrically connected to puncturing control circuit 150.

Biasing detecting switch 322 is provided in the inner wall of casing 301 to be pushed by convex part 318 provided on the side surface of puncturing needle holding section 313 when puncturing needle holding section 313 is placed in the biased position. Biasing detecting switch 322 is electrically connected to puncturing control circuit 150.

Puncturing control circuit 150 is electrically connected to solenoid 128 to control whether or not to make solenoid 128 generate a magnetic field. Puncturing control circuit 150 is mounted on substrate 330, together with radio communication section 340, and electrically connected to radio communication section 340.

Figure 5:
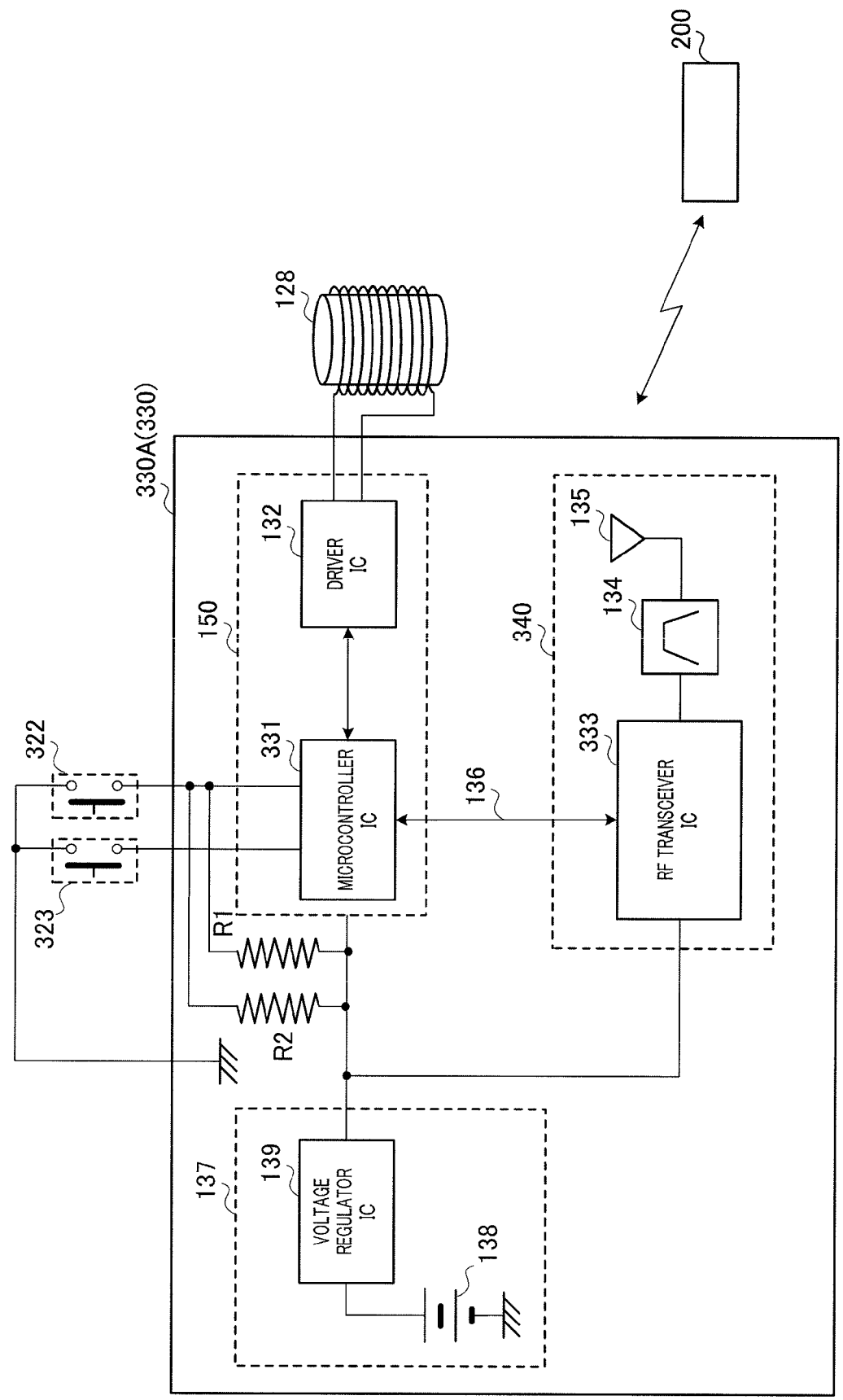
FIG. 5 is a block diagram showing an electrical circuit section in the puncturing device according to Embodiment 2.

FIG. 5 is a block diagram showing electrical circuit section 330A in puncturing device 300. Electrical circuit section 330A is formed on substrate 330. The same components as in FIG. 2 are assigned the same reference numerals and overlapping descriptions will be omitted.

As shown in FIG. 5, electrical circuit section 330A has microcontroller IC 331, driver IC 132, transceiver IC 333, filter 134, antenna 135, serial communication means 136 and power supply circuit 137.

The above-described transceiver IC 333, filter 134 and antenna 135 constitute radio communication section 340.

Microcontroller IC 331 has a general input port and detects conditions of biasing detecting switch 322 and puncturing execution button 323. R1 and R2 are pull-up resistors. R1 and R2 are set such that the input signal level of microcontroller IC 331 is "high" unless puncturing execution button 323 is pressed and biasing detecting switch 322 is turned on.

When biasing detecting switch 322 detects biasing, microcontroller IC 331 commands transceiver IC 333 in radio communication section 340 to transmit a puncturing allowing request signal to external registration device 200.

Upon receiving a signal reception interrupt request from radio communication section 340 after biasing detecting switch 322 detects puncturing needle holding section 313 being in the biased state, microcontroller IC 331 reads data stored in radio communication section 340 and decides whether or not to match the serial number registered in a memory (not shown) provided in microcontroller IC 331. When the serial number matches the serial number registered in advance, microcontroller IC 331 decides whether or not the data stored in radio communication section 340 is a puncturing allowing signal, and, when puncturing is allowed, issues a driving request to driver IC 132 upon detecting puncturing execution button 323 being pressed. Then, upon detecting puncturing execution button 322 being pressed to perform puncturing, microcontroller IC 331 issues a driving stop request to driver IC 132.

When microcontroller IC 331 issues a driving request, driver IC 132 starts supplying a driving current to solenoid 128. This driving current generates a magnetic field in the direction in which solenoid 128 generates repulsive force against permanent magnetic 127. Then, when microcontroller IC 331 issues a driving stop request, driver IC 132 stops supplying a driving current.

Transceiver IC 333 is a data transmitting and receiving IC having a function of modulation and demodulation and a function of generating error detection codes and detecting errors. At the time of transmission, transceiver IC 333 adds an error detection code to data and modulates the result, and, at the time of reception, demodulates a received signal, and then performs error detection processing on a demodulated signal and stores correctly received data in a embedded memory. Transceiver IC 333 is connected to microcontroller IC 131 in puncturing control circuit 150 by serial communication means 136 such as a UART or a SPI, and transmits and receives commands and data.

Now, the operation of puncturing device 300 configured as described above will be explained.

Figure 6:
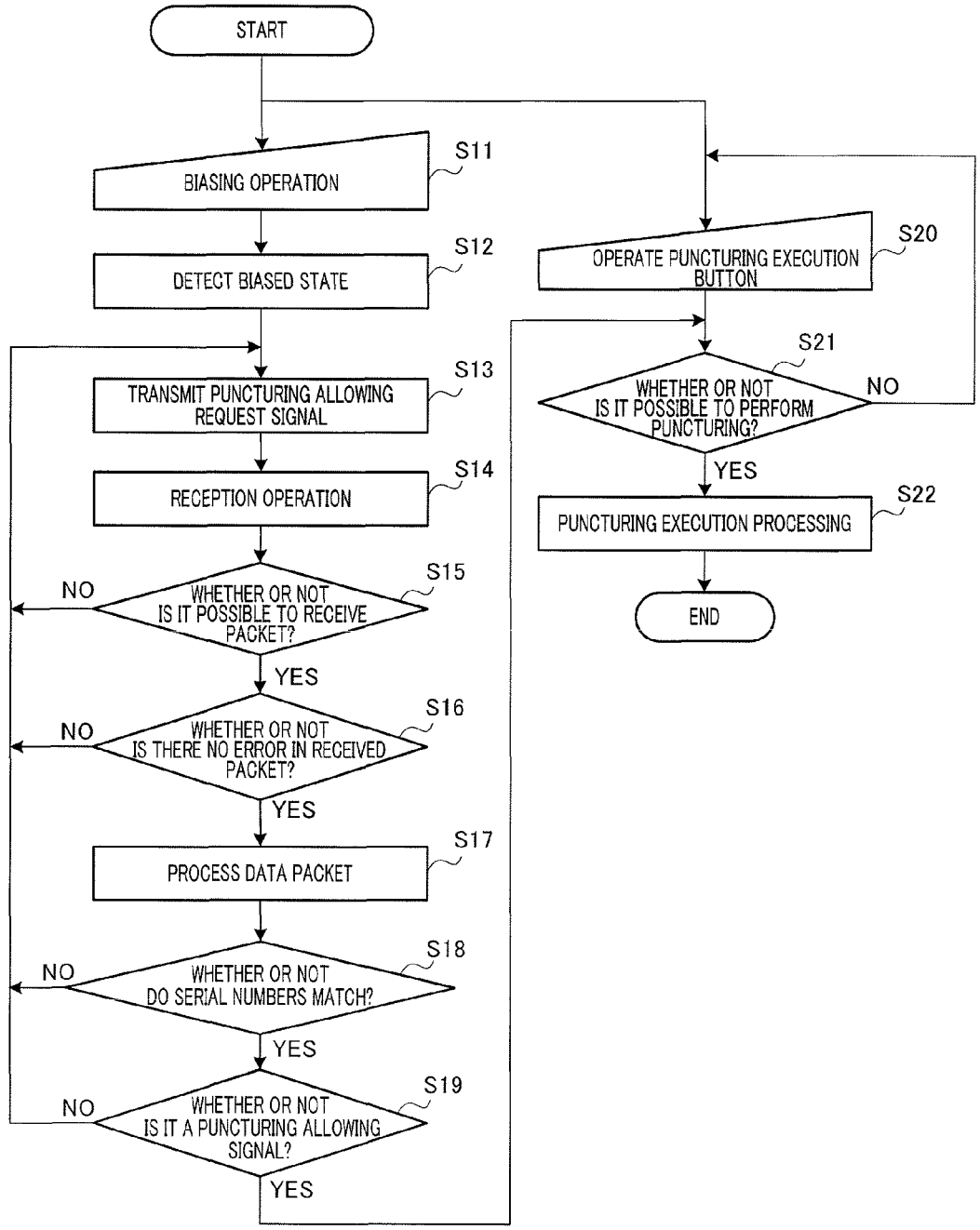
FIG. 6 is a flowchart showing processing steps from biasing operation by the user to execution of puncturing regarding the puncturing device according to Embodiment 2.

FIG. 6 is a flowchart showing processing steps from biasing operation by the user to puncturing execution in puncturing device 300.

First, in step S11, the user operates biasing operation section 315 to lock puncturing needle holding section 313 in a biased state. Convex part 318 placed on the side surface of puncturing needle holding section 313 pushes biasing detecting switch 322. By this means, the step moves to the next step S12.

In step S12, microcontroller IC 331 detects puncturing needle holding section 313 being locked in the biased state.

In step S13, microcontroller IC 331 writes data for making puncturing allowing request in the embedded memory in transceiver IC 333 and issues a data transmission request to transceiver IC 333 via serial communication means 136. Transceiver IC 333 adds an error detection code to the data written from microcontroller IC 331, and then applies modulation processing to the result, and transmits a data packet indicating puncturing allowing request to an external device, as a puncturing allowing request signal, via antenna 135.

Here, the serial number unique to puncturing device 300 is contained in advance in the data packet to be transmitted, and, even if external registration device 200 to allow this puncturing device 300 to perform puncturing receives a puncturing allowing request from a different device from puncturing device 300 registered in external registration device 200 in advance, external registration device 200 should not allow that device to perform puncturing.

In step S13, microcontroller IC 331 transmits a puncturing allowing request signal, and then moves to step S14. Microcontroller IC 331 commands transceiver IC 333 in radio communication section 340 to be placed in a receiving mode via serial communication means 136.

In step S15, transceiver IC 333 is placed in a stand-by mode for receiving a data packet, and, when receiving a data packet in a predetermined period of time, moves to step S16, and, on the other hand, when not being able to receive a data packet in a predetermined period of time, returns to step S13, retransmits a puncturing allowing request signal and enters receiving operation again.

In step S16, transceiver IC 333 performs error detection on a received data packet, and, when there is no error, moves to step S17, and, on the other hand, there is an error, returns to step S13, retransmits a puncturing allowing request signal and enters receiving operation again.

In step S17, transceiver IC 333 stores the data packet having been determined that there is no error in step 16, in the memory embedded in transceiver IC 333, and issues a signal reception interrupt to microcontroller IC 331 via serial communication means 136. Upon receiving a signal reception interrupt request from transceiver IC 333, microcontroller IC 331 reads the data packet stored in the embedded memory in transceiver IC 333 via serial communication means 136.

In step S18, microcontroller IC 331 identifies the serial number contained in the data packet. If the serial number matches the serial number registered in advance, the step moves to the next step S19. If the serial numbers do not match, microcontroller IC 331 returns to step S13, retransmits a puncturing allowing request signal and enters receiving operation again. The above-described serial number is a number unique to puncturing device 300, and contained in data in order not to mistakenly allow puncturing operation, by a puncturing allowing signal transmitted from a different puncturing device.

In step S19, microcontroller IC 331 interprets the content of the data packet and decides whether or not it is a puncturing allowing signal. If the content of the data packet represents information indicating puncturing allowing, the step moves to the next step S20. On the other hand, the content does not represent information indicating puncturing allowing, microcontroller IC 331 returns to step S13, retransmits a puncturing allowing request signal and enters receiving operation again.

In step 20, the user operates puncturing execution button 323 at a completely different timing from respective timings of the above-described step S11 to step S19, and then the step moves to step S21.

In step S21, microcontroller IC 331 decides whether or not puncturing execution button 323 is operated while a puncturing allowing signal has been received. When puncturing execution button 323 is operated while a puncturing allowing signal has been received, the step moves to step S22. If a puncturing allowing signal has not been received, the step returns to step S20 and the reoperation of puncturing execution button 323 by the user is waited for.

In step S22, microcontroller IC 331 issues a solenoid driving request to driver IC 132. Driver IC 132 supplies a driving current to solenoid 128. By this means, repulsive force works between solenoid 128 and permanent magnet 127, and therefore the locking by locking ring 123 is cancelled to perform puncturing.

As described above, according to the present embodiment, puncturing device 300 has radio communication section 340 that communicates with external registration device 200 to transmit and receive radio signals to perform radio authentication, and puncturing control circuit 150 that releases puncturing mechanism control section 320 from restricting and disallowing puncturing when radio communication section 340 provides authentication. In addition, radio communication section 340 transmits a puncturing allowing request signal to external registration device 200. Puncturing device 300 cannot perform biasing operation for puncturing unless external registration device 200 with which puncturing device 300 has been registered in the outside issues a puncturing allowing signal. For example, when external registration device 200 is a biological sample measuring apparatus, it is possible to disallow puncturing device 300 from performing puncturing operation unless the biological sample measuring apparatus (external registration device 200) resides nearby puncturing device 300. Therefore, it is possible to prevent puncturing device 300 from performing puncturing by mistake when puncturing device 300 is operated for purposes other than measurement of biological samples.

That is, biological sample measuring system 2 is used with collaboration between biological sample measuring apparatus (external registration device 200) and puncturing device 300, like in Embodiment 1. Puncturing device 300 cannot perform puncturing unless a biological sample measuring apparatus resides nearby puncturing device 300. On that condition, the biological sample measuring device measures biological samples. When a biological sample measuring apparatus outputs a puncturing allowing signal at the time to measure biological samples, it is possible to prevent a puncturing device from performing puncturing by mistake for purposes other than measurement of biological samples.

The present embodiment differs from Embodiment 1 in that, in order to disallow or restrict puncturing mechanism control section 120 from performing puncturing, charging operation is restricted in Embodiment 1, but execution of puncturing operation is restricted in the present embodiment. With the present embodiment, puncturing operation is disallowed immediately before puncturing, so that it is possible to expect an effect of even more intuitively reporting the reason for disallowing puncturing.

(Embodiment 3)

Figure 7:
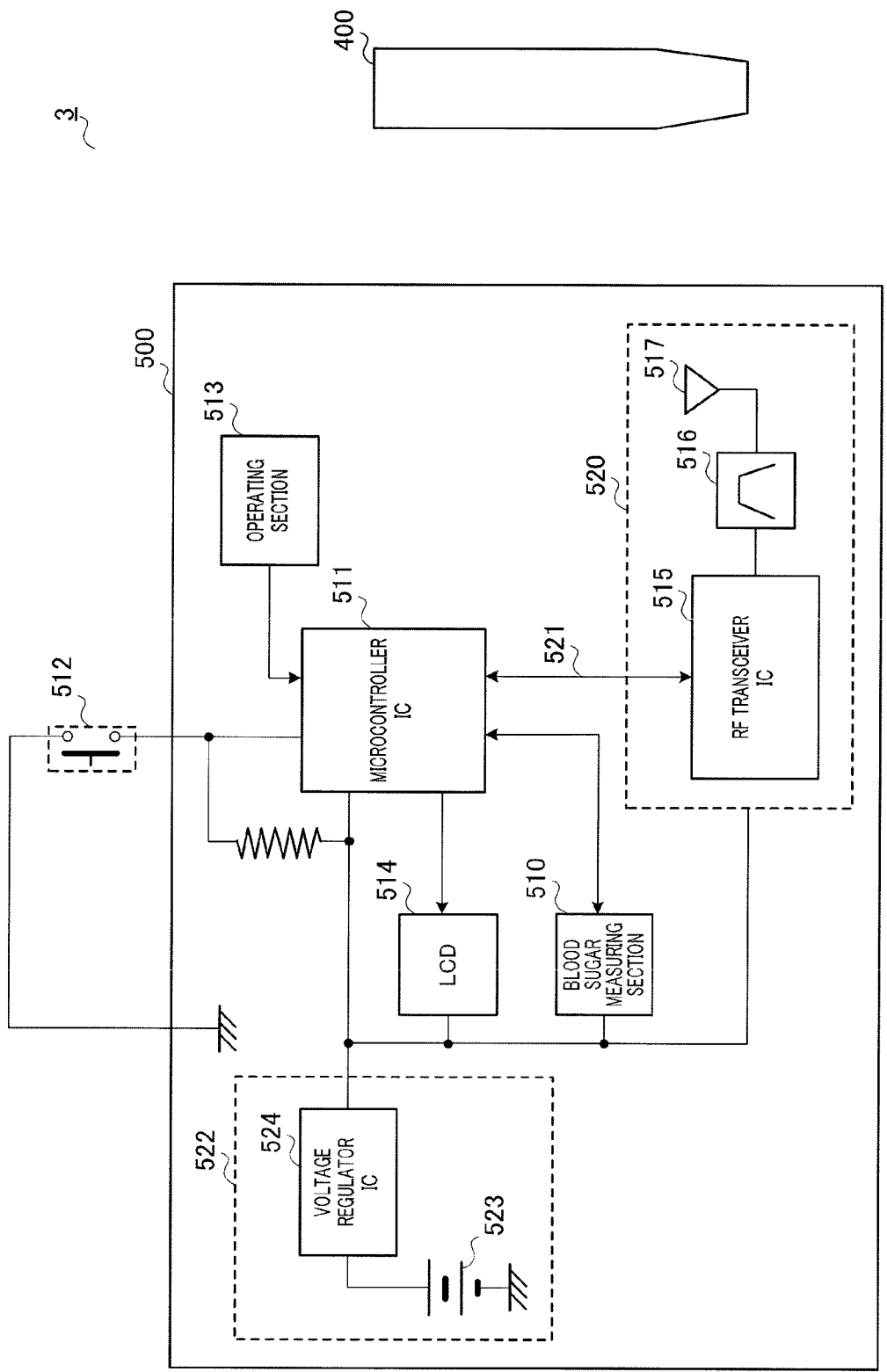
FIG. 7 is a configuration diagram showing a biological sample measuring system according to Embodiment 3 of the present invention.

FIG. 7 is a configuration diagram showing a biological sample measuring system according to Embodiment 3 of the present invention.

As shown in FIG. 7, biological sample measuring system 3 is composed of puncturing apparatus 400 and biological sample measuring apparatus 500.

Puncturing apparatus 400 may be either puncturing device 100 according to Embodiment 1 or puncturing device 300 according to Embodiment 2.

Biological sample measuring apparatus 500 is not limited as long as it is a measuring apparatus that measures biological samples. With the present embodiment, blood sugar meter 500 that measures blood sugar levels, is used as an example of biological sample measuring apparatus 500.

In addition, biological sample measuring apparatus 500 has a radio communication section 520 that transmits a puncturing allowing signal to puncturing device 100 or puncturing device 300 when blood sugar measuring section 510 is ready to perform measurement.

As shown in FIG. 7, blood sugar meter 500 is a blood sugar measuring device that performs measurement by diabetes patients by themselves to determine the dosage of insulin and to control blood sugar levels on a daily basis. When using blood sugar meter 500, a diabetes patient performs the operation including puncturing the patient's finger tip using puncturing apparatus 400 to sample blood, and depositing this blood, in a spot, on a specimen (not shown) inserted in blood sugar meter 500.

Blood sugar meter 500 has blood sugar measuring section 510 (biological sample measuring section), microcontroller IC 511, insertion detecting switch 512, operating section 513, display section (LCD) 514, RF transceiver IC 515, filter 516, antenna 517, serial communication means 521 and power supply circuit 522.

The above-mentioned RF transceiver IC 515, filter 516 and antenna 517 constitute radio communication section 520.

Blood sugar measuring section 510 is controlled by microcontroller IC 511. The configuration of blood sugar measuring section 510 is disclosed, for example, in FIG. 31 and so forth in WO2005-054840.

Insertion detecting switch 512 detects a specimen being inserted and outputs a detection signal to microcontroller IC 511. To be more specific, insertion detecting switch 512 is connected to an interrupt input port in microcontroller IC 511. When insertion detecting switch 12 is pushed by inserting the specimen, microcontroller IC 511 receives an activation interrupt request and awakes from a sleep mode. Microcontroller IC 511 awakes from a sleep mode, so that blood sugar meter 500 is ready to measure blood sugar levels.

Operating section 513 is, for example, a push switch. Operating section 513 is connected to an input port in microcontroller IC 511. Using operating section 513, the user performs operation on microcontroller IC 511, including reading past measurement results and change in setting of blood sugar meter 500.

Display section 514 is composed of, for example, a liquid crystal display and a driver. Display section 514 is controlled by microcontroller IC 511 and displays measured blood sugar levels and time information such as date.

RF transceiver IC 515 is a data transmitting and receiving IC having a function of modulation and demodulation, and a function of generating error detecting codes and detecting errors. At the time of transmission, RF transceiver IC 515 adds an error detection code to data and modulates the result, and, at the time of reception, demodulates a received signal, and then performs error detection processing on a demodulated signal, and stores correctly received data in an embedded memory. RF transceiver IC 515 communicates with microcontroller IC 511 to transmit and receive commands and data through serial communication means 521.

Filter 516 is inserted between RF transceiver IC 515 and antenna 517 in order to reduce out-of-band radiation at the time of transmission and reduce interference of out-of-band radio waves at the time of reception.

Antenna 517 is a small chip antenna made of, for example, a high dielectric material.

Serial communication means 521 is, for example, a UART or a SPI.

Power supply circuit 522 is composed of, for example, dry battery 523 and voltage regulator IC 524. Power supply circuit 522 supplies power to blood sugar measuring section 510, display section 514, microcontroller IC 511 and radio communication section 520.

Now, the operation of a biological sample measuring system configured as described above, will be explained.

First, the operation of blood sugar meter 500 will be explained in a case in which puncturing device 100 according to Embodiment 1 is adopted as the above-described puncturing apparatus 400.

Figure 8:
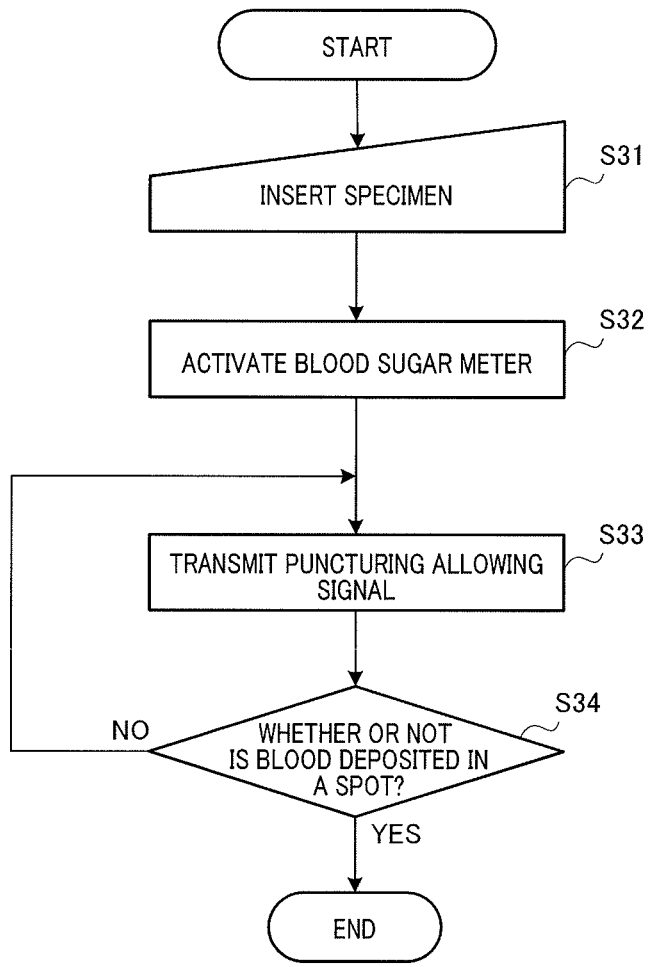
FIG. 8 is a flowchart showing processing steps regarding a blood sugar meter according to Embodiment 3.

FIG. 8 is a flowchart showing processing steps in blood sugar meter 500 and shows operation after blood sugar meter 500 transmits a puncturing allowing signal to puncturing apparatus 400 until measuring a blood sugar level.

First, in step S31, when the user inserts a specimen in blood sugar meter 500, the specimen pushes insertion detecting switch 512.

In step S32, microcontroller IC 511 detects insertion detecting switch 512 being pushed and awakes from a sleep mode. By this means, blood sugar meter 500 is ready to perform measurement, and the step moves to step S33.

In step S33, microcontroller IC 511 writes data for allowing puncturing in an embedded memory in RF transceiver IC 515 via serial communication means 521. Then, microcontroller IC 511 issues a data transmission request to RF transceiver IC 515. RF transceiver IC 515 adds an error detection code to the data written from microcontroller IC 511, and then applies modulation processing to the result, and transmits a data packet indicating allowing puncturing to puncturing apparatus 400 via antenna 517.

The serial number unique to puncturing apparatus 400 contained in advance in the data packet to be transmitted in order not to mistakenly allow an irrelevant puncturing device to perform puncturing.

After a puncturing allowing signal is transmitted in the above step S33, the step moves to step S34.

In step S34, microcontroller IC 511 decides whether or not blood is deposited on a specimen in a spot, based on the measurement result from blood sugar measuring section 510. In addition, during this time, puncturing apparatus 400 receives a puncturing allowing signal. The user performs puncturing using puncturing apparatus 400 having received the puncturing allowing signal, and deposits blood on a specimen in a spot.

When detecting blood being deposited on the specimen in a spot, microcontroller IC 511 determines that puncturing has been performed in puncturing apparatus 400 and stops transmitting a puncturing allowing signal. Then, blood sugar measuring section 510 performs measurement of the blood sugar level of blood deposited on the specimen in a spot (not shown).

On the other hand, when it is not possible to detect blood being deposited in a spot, the step returns to step S33 and microcontroller IC 511 retransmits a puncturing allowing signal.

Here, it is determined to return the step from step S34 to step S33 in order to perform retransmission, for example, after ten seconds, taking into account the period of time required for actions including puncturing and depositing in a spot by the user.

Blood sugar meter 500 operates in the above-described steps.

With Embodiment 1, the basic operation of puncturing apparatus 400 when receiving a puncturing allowing signal, has been described.

As supplementary explanation, puncturing apparatus 400 is in a stand-by mode to wait for a puncturing allowing signal after turnon of power. Upon receiving a puncturing allowing signal transmitted from blood sugar meter 500 after a specimen is mounted in blood sugar meter 500, puncturing apparatus 400 releases from disallowing puncturing apparatus 400 from performing biasing operation, and therefore can perform puncturing.

Next, the operation of blood sugar meter 500 in a case in which puncturing device 300 according to Embodiment 2 is adopted as the above-described puncturing apparatus 400.

Figure 9:
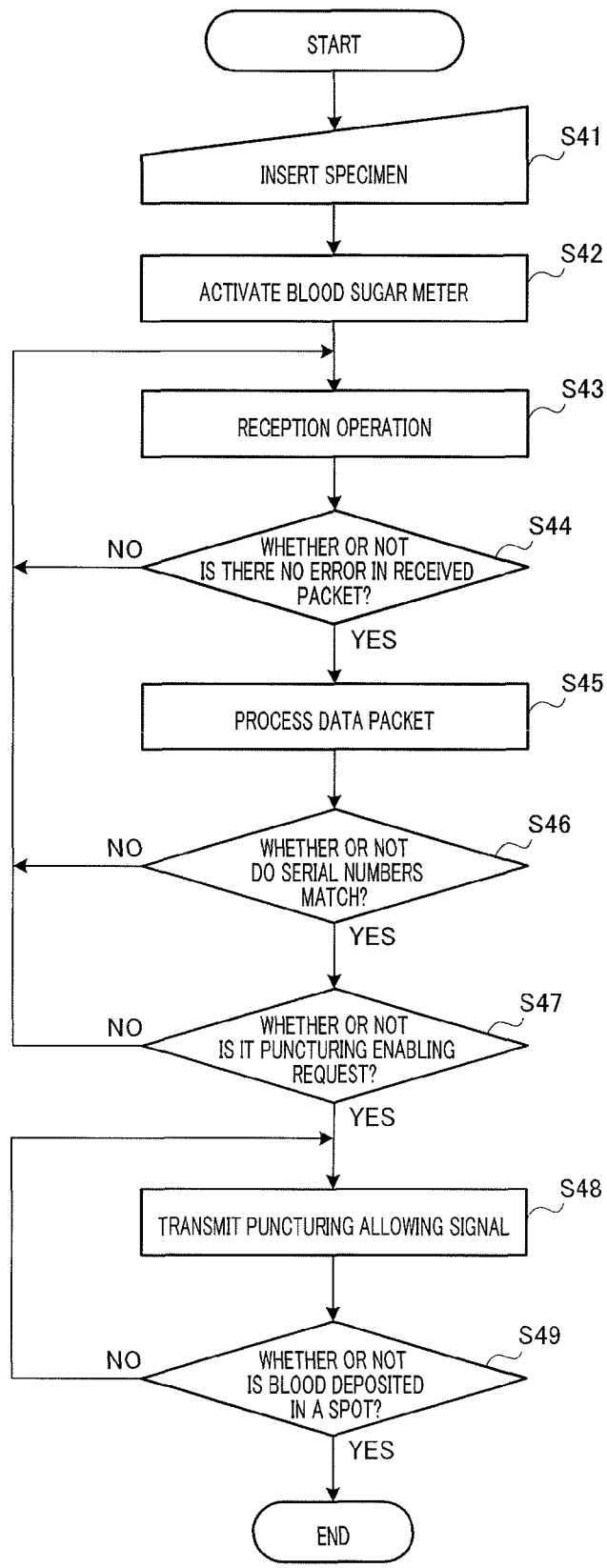
FIG. 9 is a flowchart showing the operation of the blood sugar meter when a puncturing apparatus according to Embodiment 3 generates a puncturing allowing request signal.

FIG. 9 is a flowchart showing the operation of blood sugar meter 500 when puncturing apparatus 400 sends a puncturing allowing request signal.

First, in step S41, when the user inserts a specimen in blood sugar meter 500, the specimen pushes insertion detecting switch 512.

In step S42, microcontroller IC 511 detects insertion detecting switch 512 being pushed and awakes from a sleep mode. By this means, blood sugar meter 500 is ready to perform measurement, and the step moves to step S43.

In step S43, microcontroller IC 511 commands RF transceiver IC 515 to be placed in a receiving mode, via serial communication means 521. RF transceiver IC 515 receives a data packet transmitted from puncturing apparatus 400 via antenna 517.

In step S44, microcontroller IC 511 performs error detection on the data packet received by RF transceiver IC 515, and, when there is no error, the step moves to step S45. When there is an error, microcontroller IC 511 returns to step S43 and continues the receiving operation.

Before that, biasing operation to perform puncturing in puncturing apparatus 400 has been performed, puncturing apparatus 400 has sent a puncturing allowing request signal.

In step S45, RF transceiver IC 515 stores the data packet having been determined that there is no error in step S44, in a memory embedded in RF transceiver IC 515 and issues a signal reception interrupt to microcontroller IC 511 via serial communication means 521. Upon receiving a signal reception interrupt request from RF transceiver IC 515, microcontroller IC 511 reads the data packet stored in the embedded memory in RF transceiver IC 515, via serial communication means 521.

In step S46, microcontroller IC 511 identifies the serial number contained in the data packet. When the serial number matches the serial number registered in advance, microcontroller IC 511 moves to the next step S47. When the serial numbers do not match, microcontroller IC 511 returns to step S43 and continues the receiving operation. The above-described serial number is a number unique to puncturing apparatus 400. The number unique to puncturing apparatus 400 is adopted as the above-described serial number in order not to allow puncturing requested from any different puncturing apparatus from puncturing apparatus 400 registered in blood sugar meter 500 in advance.

In step S47, microcontroller IC 511 interprets the content of the data packet and decides whether or not the content represents a puncturing allowing request signal. When the content of the data packet represents a puncturing allowing request signal, microcontroller IC 511 moves to the next step S48. On the other hand, the content represents information other than a puncturing allowing signal, microcontroller IC 511 returns to step S43 and continues the receiving operation.

In step S48, microcontroller IC 511 writes data for allowing puncturing in the embedded memory in RF transceiver IC 515 and issues a data transmission request to RF transceiver IC 515, using serial communication means 521. RF transceiver IC 515 adds an error detection code to the data written from microcontroller IC 511, and then applies modulation processing to the result, and transmits a data packet indicating allowing puncturing to puncturing apparatus 400, via antenna 517.

The serial number unique to puncturing apparatus 400 transmitting a puncturing allowing request signal, is contained in advance in the data packet to be transmitted, in order not to mistakenly allow an irrelevant puncturing device to perform puncturing when the irrelevant puncturing device receives a puncturing allowing signal.

After a puncturing allowing signal is transmitted in the above step S48, the step moves to step S49.

In step S49, microcontroller IC 511 decides whether or not blood has been deposited on a specimen in a spot, based on the measurement result from blood sugar measuring section 510. In addition, during this time, puncturing apparatus 400 receives a puncturing allowing signal. The user performs puncturing using puncturing apparatus 400 having received the puncturing allowing signal, and deposits blood on a specimen in a spot.

When detecting blood being deposited on the specimen in a spot, microcontroller IC 511 determines that puncturing has been performed in puncturing apparatus 400 and stops transmitting a puncturing allowing signal. Then, blood sugar measuring section 510 measures the blood sugar level of blood deposited on the specimen in a spot (not shown).

On the other hand, when it is not possible to detect blood having been deposited in a spot, microcontroller IC 511 returns to step S48 and retransmits a puncturing allowing signal.

Here, it is determined to return the step from step S49 to step S48 in order to perform retransmission, for example, after ten seconds, taking into account the period of time required for actions including puncturing and depositing in a spot by the user.

Blood sugar meter 500 operates in the above-described steps.

The basic operation of puncturing apparatus 400 when receiving a puncturing allowing signal have already been explained with Embodiment 2.

As described above, according to the present embodiment, blood sugar meter 500 has radio communication section 520 that transmits a puncturing allowing signal to puncturing device 100 or puncturing device 300 when blood sugar measuring section 510 is ready to perform measurement. It is possible to disallow puncturing device 100 or 300 from performing puncturing operation unless blood sugar meter 500 resides nearby puncturing device 100 or 300 and is ready to perform measurement. Therefore, it is possible to prevent puncturing device 100 or 300 from performing puncturing by mistake when puncturing device 100 or 300 is operated for purposes other than measurement of biological samples.

That is, biological sample measuring system 3 is used with collaboration between biological sample measuring apparatus (blood sugar meter 500) and puncturing device 100 or 300, like in Embodiments 1 and 2. Puncturing device 100 or 300 cannot perform puncturing unless a biological sample measuring apparatus resides nearby puncturing device 100 or 300. On that condition, the biological sample measuring device measures biological samples. A biological sample measuring apparatus outputs a puncturing allowing signal when measuring biological samples, so that it is possible to prevent mistaken puncturing for purposes other than measurement of biological samples.

In addition to the above-described advantages, there are the following advantages. By the above-described configurations and operation, it is not possible to perform puncturing using a puncturing apparatus unless a specimen is inserted in a biological sample measuring apparatus, so that it is possible to prevent the user from performing puncturing using a puncturing apparatus despite forgetting to insert a specimen. Blood from a finger tip is sampled using a puncturing apparatus in order to measure blood sugar levels, and, when the user attempts to insert the specimen after puncturing in a biological sample measuring apparatus, blood from the finger tip adheres on the biological sample measuring apparatus and clothes, so that it is not preferable from a hygiene standpoint.

That is, it is possible to avoid this hygienic problem using the puncturing device and the biological sample measuring system according to the present embodiment.

In addition, in recent years, it is possible to measure a blood sugar level even by a small amount of blood, so that the depth of puncturing is shallow to reduce the amount of blood to. Therefore, when the user inserts a specimen in a biological sample measuring apparatus and prepares for measurement of the blood sugar level after performing puncturing, blood dries during this time, and consequently is not likely to be sampled unless puncturing is performed again. By using the puncturing device and the biological sample measuring system according to the present embodiment, it is possible to avoid this problem.

Here, with the present embodiment, although a case has been shown as an example where, after microcontroller IC 511 in blood sugar meter 500 awakes from a sleep mode by inserting a specimen, radio communication section 520 transmits a puncturing allowing signal (step S33) or radio communication section 520 enters receiving operation (step S43), the present invention is not limited to this.

For example, even if microcontroller IC 511 in blood sugar meter 500 is not placed in a sleep mode but in a normal operating mode, the above-described steps S33 and S34 should not be performed unless a specimen is inserted. Then, when microcontroller IC 511 is placed in a normal operating mode and detects a specimen being inserted, steps S33 and S43 may be performed. Blood sugar meter 500 is not limited as long as it issues a puncturing allowing signal as a trigger that a specimen has been inserted.

(Embodiment 4)

With Embodiments 1 to 3, the puncturing device that restricts biasing operation (charging) or restricts puncturing according to a radio signal, has been described.

A radio signal may be an RF-ID (radio frequency-identification) signal, and this example will be described with Embodiments 4 and 5.

Figure 10:
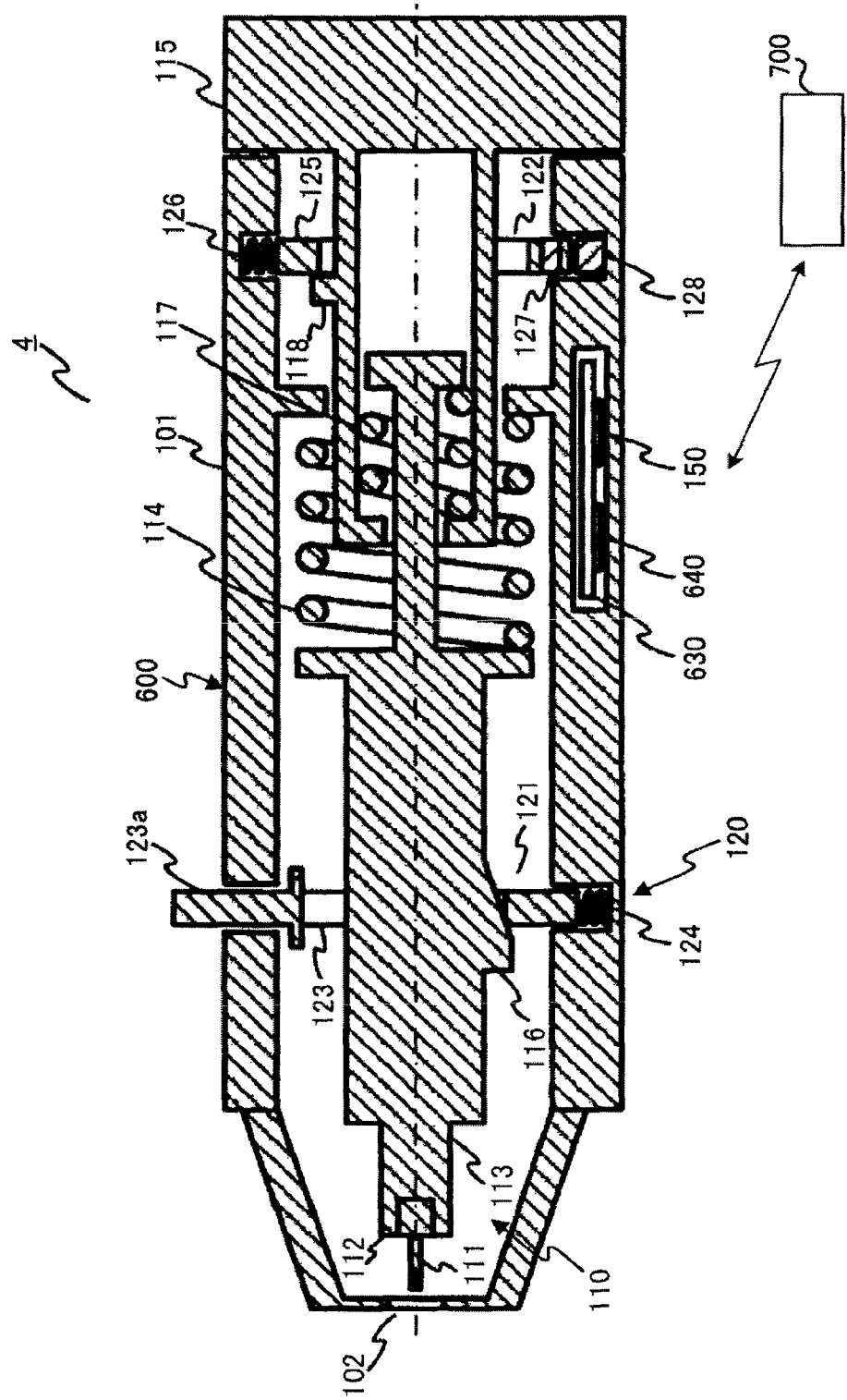
FIG. 10 is a cross sectional view showing a puncturing device according to Embodiment 4 of the present invention.

FIG. 10 is a cross sectional view showing a puncturing device according to Embodiment 4 of the present invention. To explain the present embodiment, the same components as in FIG. 1 are assigned the same reference numerals, and overlapping descriptions will be omitted.

As shown in FIG. 10, biological sample measuring system 4 has puncturing device 600, and IC card 700 that communicates with puncturing device 600 by RF-ID to transmit and receive puncturing allowing signals.

Puncturing device 600 has casing 101, puncturing mechanism 110, puncturing mechanism control section 120, substrate 630 arranged in casing 101, and RF-ID radio communication section 640 and puncturing control circuit 150 placed on substrate 630.

Puncturing device 600 has RF-ID communication section 640 on substrate 630, instead of radio communication section 140 in puncturing device 100 in FIG. 1.

Figure 11:
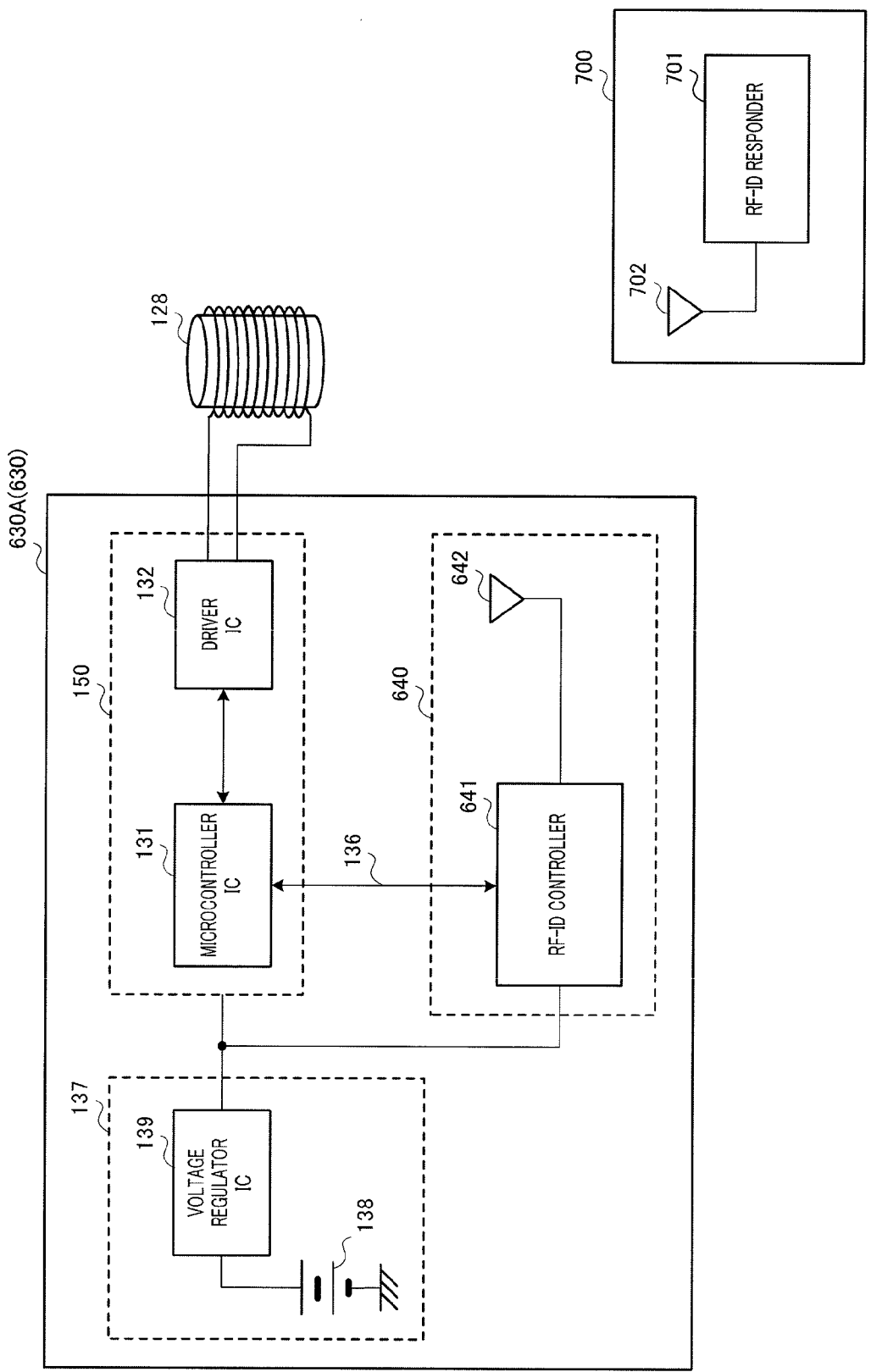
FIG. 11 is a block diagram showing an electrical circuit section and an IC card in the puncturing device according to Embodiment 4.

FIG. 11 is a block diagram showing electrical circuit section 630A in puncturing device 600 and IC card 700.

Electrical circuit section 630A is formed on substrate 630. The same components as in FIG. 2 are assigned the same reference numerals and overlapping descriptions will be omitted.

As shown in FIG. 11, electrical circuit section 630A has microcontroller IC 131, driver IC 132, RF-ID communication section 640, serial communication means 136 and power supply circuit 137.

RF-ID communication section 640 is composed of RF-ID controller 641 and RF-ID antenna 642.

IC card 700 is composed of RF-ID responder IC 701 and RF-ID antenna 702 to communicate with RF-ID communication section 640.

RF-ID communication section 640 serves as an RF-ID reader/writer.

RF-ID responder IC 701 records at least the serial number and the puncturing allowing flag on its embedded memory (not shown).

Now, the operation of a biological sample measuring system configured as described above will be explained.

When puncturing device 600 is turned on, microcontroller IC 131 requests RF-ID controller 641 to communicate with IC card 700, via serial communication means 136. Then, RF-ID controller 641 enters a stand-by mode and waits for a response from IC card.

In a case of a system that performs passive RF-ID communication, this standby refers to a state in which RF-ID antenna 642 emits radio waves in a very short distance. When IC card 700 approaches the coverage of the emitted radio waves, the radio waves are rectified by a rectifier circuit (not shown) provided in RF-ID antenna 702 in IC card 700 and supplied to RF-ID responder IC 701, as an electromotive current. RF-ID antenna 702 reads the content (in this case, the serial number and the puncturing allowing flag) recorded in RF-ID responder IC 701, converts the content into radio waves and emits them.

In this way, when response radio waves are emitted from RF-ID antenna 702 in IC card 700, RF-ID antenna 642 receives these radio waves. RF-ID controller 641 reads the above-described serial number and puncturing allowing flag, from the radio waves received by RF-ID antenna 642, and transmits an interrupt request to microcontroller IC 131 via serial communication means 136.

Upon receiving the interrupt request from RF-ID communication section 640, microcontroller IC 131 reads data stored in RF-ID communication section 640 and decides whether or not to match the serial number registered in a memory (not shown) provided in microcontroller IC 131.

When the serial number matches the serial number registered in advance, microcontroller IC 131 also decides whether or not the data stored in RF-ID communication section 640 is a puncturing allowing signal, and, when it is a puncturing allowing signal, issues a driving request to driver IC 132. Subsequent operation of puncturing device 600 are the same as steps following step S5 in FIG. 3 in Embodiment 1.

On the other hand, when microcontroller IC 131 decides whether or not to match the serial number and allow puncturing, and, if either one does not satisfy the requirement, microcontroller IC 131 requests again RF-ID controller 641 to perform communication again.

As described above, puncturing device 600 according to the present embodiment is configured to decide whether or not to allow biasing and puncturing by authentication using RF-ID after turnon of power, and therefore cannot perform biasing operation for puncturing unless IC card 700 which is registered and paired with puncturing device 600 approaches puncturing device 600. That is, puncturing device 600 cannot perform puncturing unless the user having IC card 700 registered with puncturing device 600 performs authentication when measuring biological samples, so that it is possible to prevent puncturing device 600 from performing puncturing by mistake when puncturing device 600 is operated for purposes other than measurement of biological samples.

Here, although a case has been explained as an example where puncturing device 600 has RF-ID communication section 640 instead of communication section 140 in puncturing device 100 according to Embodiment 1, another case is possible where RF-ID communication section 640 is provided instead of radio communication section 340 in puncturing device 300 according to Embodiment 2.

In puncturing device 300 shown in Embodiment 2, radio communication section 340 transmits a puncturing allowing request to perform puncturing after the user performs biasing operation. This operation to transmit a puncturing allowing request may be replaced with the operation to place RF-ID controller 641 in a stand-by mode, as shown in the present embodiment.

To be more specific, radio communication section 340 in puncturing device 300 according to Embodiment 2 is replaced with RF-ID communication section 640 shown in the present embodiment. Then, when microcontroller IC 131 issues a puncturing allowing request to RF-ID controller 641, via serial communication means 136, RF-ID controller 641 enters a stand-by mode and waits for a response from IC card 700. The following operation is the same as the puncturing operation according to Embodiment 2 and the operation of RF-ID communication section 640 shown in the present embodiment.

By configurations described above, it is not possible to perform puncturing unless the user having registered IC card 700 identifies RF-ID after puncturing device 300 performs biasing operation for puncturing, so that it is possible to prevent puncturing device 300 from puncturing by mistake even if puncturing device 300 is operated for purposes other than measurement of biological samples.

Here, with the present embodiment, although a case has been shown as an example where authentication of RF-ID is performed using an IC card having an RF-ID antenna, the present invention is not limited to IC cards, and another case is possible where an RF-ID antenna is provided in belongings that the user always possesses, for example, a mobile telephone, a wrist watch, a blood sugar meter and other portable medical equipment, and thereby it is possible to improve convenience.

As described above, an advantage of use of RF-ID communication is that the communication distance is very short even if this RF-ID communication is non-contact communication. By using this advantage of RF-ID communication, it is possible to allow puncturing more appropriately.

(Embodiment 5)

Figure 12:
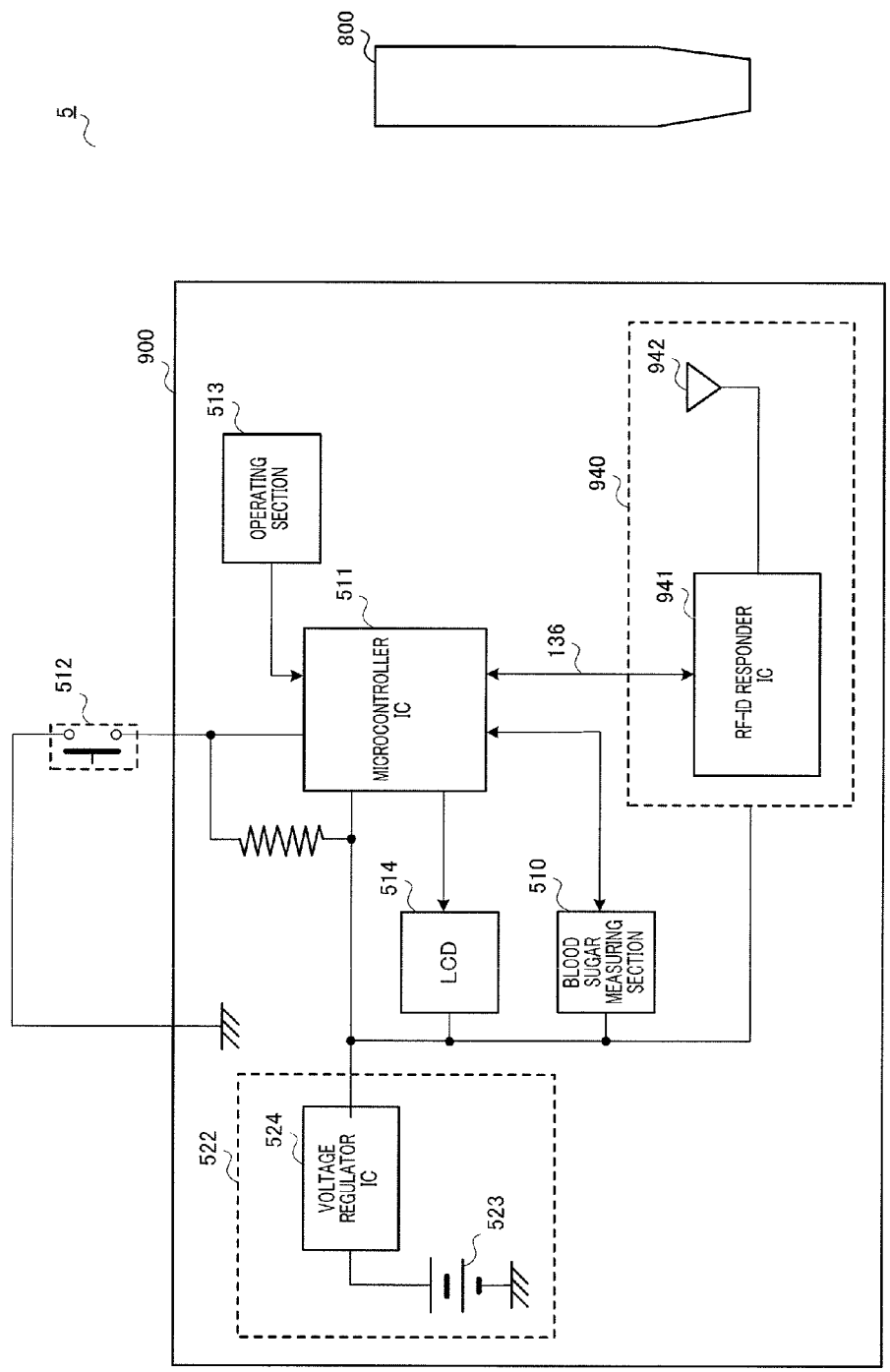
FIG. 12 shows a configuration of a biological sample measuring system according to Embodiment 5 of the present invention.

FIG. 12 shows a configuration of a biological sample measuring system according to Embodiment 5 of the present invention. To explain the present embodiment, the same components as in FIG. 7 and FIG. 11 are assigned the same reference numerals and overlapping descriptions will be omitted.

As shown in FIG. 12, biological sample measuring system 5 is composed of puncturing apparatus 800 and biological sample measuring apparatus 900.

Puncturing apparatus 800 is the same as puncturing device 600 in Embodiment 4.

Biological sample measuring apparatus 900 is not limited as long as it is a measuring apparatus that measures biological samples. With the present embodiment, blood sugar meter 900 that measures blood sugar levels, is used as an example of biological sample measuring apparatus 900.

Blood sugar meter 900 varies from blood sugar meter 500 shown in FIG. 7 in that RF-ID communication section 940 shown in FIG. 11 is used instead of radio communication section 520 in blood sugar meter 500.

RF-ID communication section 940 is composed of RF-ID responder IC 941 and RF-ID antenna 942.

RF-ID communication section 940 varies from IC card 700 shown in FIG. 11 in that it is possible to switch puncturing allowing information in a memory embedded in RF-ID responder IC 941 between allowing puncturing and disallowing puncturing. This switching is performed by microcontroller IC 511 in blood sugar meter 900. Here, the serial number is stored in the memory (not shown) in RF-ID responder IC 941, like in IC card 700 shown in FIG. 11.

Now, switching between allowing puncturing and disallowing puncturing in the biological sample measuring system configured as described above, will be explained.

First, when blood sugar meter 900 is activated by turnon of power, or awakes from a sleep mode, puncturing allowing information stored in the memory embedded in RF-ID responder IC 941 has been a puncturing disallowing signal. This is controlled by microcontroller IC 511 in blood sugar meter 900, based on input and so forth from operating section 513.

When insertion detecting switch 512 is pushed by inserting a specimen, microcontroller IC 511 switches puncturing allowing information stored in the memory embedded in RF-ID responder IC 941 to a puncturing allowing signal, via serial communication means 136. When blood sugar meter 900 is in a sleep mode at this time, operation to switch to a puncturing allowing signal is performed after canceling the sleep mode.

When blood of the user is deposited on the inserted specimen in a spot, blood sugar measuring section 510 measures the blood sugar level. Microcontroller IC 511 switches puncturing allowing information stored in the memory embedded in RF-ID responder IC 941, to a puncturing disallowing signal.

That is, only during measurement of the blood sugar level after a specimen is inserted in blood sugar meter 900, RF-ID responder IC 941 holds a puncturing allowing signal, or, otherwise, holds a puncturing disallowing signal and sends responses in RF-ID communication.

Next, the operation of the biological sample measuring system, including puncturing apparatus 800, will be explained.

Puncturing apparatus 800 is the same as puncturing device 600 shown in Embodiment 4. First, a case (equivalent to Embodiment 1) will be explained where biasing operation for puncturing is restricted.

The user prepares puncturing apparatus 800, blood sugar meter 900 and a specimen. Then, first, puncturing apparatus 800 is turned on. Then, puncturing apparatus 800 places RF-ID controller 641 (see FIG. 11, and the same shall apply hereinafter) in a stand-by mode to wait for. At this time, a specimen has not been inserted in blood sugar meter 900 yet. Accordingly, even if blood sugar meter 900 is approached to puncturing apparatus 800, a signal received by RF antenna 642 (see FIG. 11, and the same shall apply hereinafter) contains a puncturing disallowing signal, so that puncturing apparatus 800 cannot perform biasing operation.

Next, when a specimen is inserted in blood sugar meter 900, microcontroller IC 511 switches puncturing allowing information in RF-ID responder IC 941 from a puncturing disallowing signal to a puncturing allowing signal. After that, when blood sugar 900 approaches puncturing apparatus 800, a signal received by antenna 942 contains a puncturing allowing signal, so that puncturing apparatus 800 can perform biasing operation.

Then, when the user performs puncturing and deposits blood on the specimen inserted in blood sugar meter 900, in a spot, microcontroller IC 511 (see FIG. 12) switches puncturing allowing information in RF-ID responder IC 941 from a puncturing allowing signal to a puncturing disallowing signal, so that puncturing apparatus 800 cannot perform biasing operation again.

Here, if a specimen has been inserted in blood sugar meter 900 before the user turns on puncturing apparatus 800, puncturing apparatus 800 is turned on and blood sugar meter 900 approaches puncturing apparatus 800 to allow puncturing apparatus 800 to perform puncturing operation. Anyway, this is operation by the user in order to measure the blood sugar level, and it is still possible to prevent a puncturing apparatus from puncturing by mistake for purposes other than measurement of biological samples.

Next, a case (equivalent to Embodiment 2) will be explained where puncturing apparatus 800 can perform biasing operation freely, but is restricted to perform puncturing operation.

The user prepares puncturing apparatus 800, blood sugar meter 900 and a specimen. Then, first, puncturing apparatus 800 is turned on, and then performs biasing operation. Then, puncturing apparatus 800 places RF-ID controller 941 in a stand-by mode to wait for. At this time, a specimen has not been inserted in blood sugar meter 900 yet. Therefore, even if blood sugar meter 900 approaches puncturing apparatus 800, a signal received by antenna 942 contains a puncturing disallowing signal, so that puncturing apparatus 800 cannot perform puncturing operation.

Next, when a specimen is inserted in blood sugar meter 900, microcontroller IC 511 switches puncturing allowing information in RF-ID responder IC 701 (see FIG. 11) from a puncturing disallowing signal to a puncturing allowing signal.

Then, when blood sugar meter 900 approaches puncturing apparatus 800, a signal received by antenna 942 contains a puncturing allowing signal, so that puncturing apparatus 800 can perform puncturing operation.

Then, when the user performs puncturing and deposits blood on the specimen inserted in blood sugar meter 900, in a spot, microcontroller IC 511 switches puncturing allowing information in RF-ID responder IC 701 from a puncturing allowing signal to a puncturing disallowing signal, so that puncturing apparatus 800 cannot perform puncturing operation again.

Here, when the user has inserted a specimen in blood sugar meter 900 before turning on puncturing apparatus 800, puncturing apparatus 800 is turned on and blood sugar meter 900 approaches puncturing apparatus 800 to allow puncturing apparatus 800 to perform puncturing operation. Anyway, this is operation by the user in order to measure the blood sugar level, and it is still possible to prevent a puncturing apparatus from puncturing by mistake for purposes other than measurement of biological samples.

As described above, according to the present embodiment, in biological sample measuring system 5, puncturing apparatus 800 cannot perform puncturing unless a biological sample measuring apparatus (blood sugar meter 900) resides nearby puncturing apparatus 800 and is used to measure blood sugar levels (biological samples), so that it is possible to prevent puncturing apparatus 800 from puncturing by mistake when puncturing apparatus 800 is operated for purposes other than measurement of biological samples.

With the present embodiment, the invention has a feature that, particularly, puncturing allowing information read by RF-ID communication, that is, puncturing allowing information in blood sugar meter 900 is switched between allowing and disallowing depending on whether or not a specimen is inserted, and thereby it is possible to achieve the specific advantage described in Embodiment 3.

The above description is illustration of preferred embodiments of the present invention and the scope of the invention is not limited to this.

With each of the above-described embodiments, a case is possible where, after a puncturing device or puncturing apparatus receives a puncturing allowing signal and is placed in a state in which puncturing (biasing operation) is allowed, puncturing (biasing operation) may be automatically cancelled if a puncturing device or puncturing apparatus does not perform puncturing operation or biasing operation, or does not receive a puncturing disallowing signal after a certain period of time has passed. That is, it is preferable to provide a timer in the microcontroller IC in a puncturing device or puncturing apparatus to control puncturing (biasing operation) by measuring the passage of this certain period of time.

By this means, even if the user does not perform puncturing for some reason after puncturing (biasing operation) is allowed once, the allowed puncturing (biasing operation) is cancelled after a certain period of time has passed, so that it is possible to prevent mistaken puncturing for purposes other than measurement of biological samples.

Although the names "biological sample measuring apparatus" and "biological sample measuring system" are used in each of the above-described embodiment for ease of explanation, "blood sugar level measuring apparatus", "puncturing unit" and so forth are possible naturally. In addition, an external registration device may also be referred to as "external device" or "radio communication unit."

Moreover, the type, the number, the connection method and so forth of components, for example, for restricting and disallowing puncturing, are not limited.

The disclosure of Japanese Patent Application No. 2009-034969, filed on Feb. 18, 2009, including the specification, drawings and abstract, is incorporated herein by reference in its entirety.

INDUSTRIAL APPLICABILITY

The puncturing device, measuring apparatus and measuring system according to the present invention have the function of preventing mistaken use by means of a radio communication function, and are useful for a biological sample measuring system and so forth that need to sample blood by puncturing. In addition, it is expected to widely spread for use with various measuring apparatuses or puncturing apparatuses.

REFERENCE SIGNS LIST

1, 2, 3, 4, 5 Biological sample measuring system
100, 300, 600 Puncturing device
110, 310 Puncturing mechanism
111 Puncturing needle
113, 313 Puncturing needle holding section
114 Biasing spring
115, 315 Biasing operation section
120, 320 Puncturing mechanism control section
121 Locking mechanism
122 Biasing control mechanism
123 Locking ring
124 Locking ring spring
127 Permanent magnet
128 Solenoid
130, 330, 630 Substrate
130A, 330A, 630A Electrical circuit section
131, 331, 511 Microcontroller IC
132 Driver IC 133 Receiver IC
134, 516 Filter
135, 517 Antenna
136, 521 Serial communication means
137 Power supply circuit
140, 340, 520 Radio communication section
150 Puncturing control circuit
200 External registration device
321 Locking control mechanism
323 Puncturing execution button
400, 800 Puncturing apparatus
500, 900 Blood sugar meter (biological sample measuring apparatus)
510 blood sugar measuring section
512 Insertion detecting switch
513 Operating section
514 Display section (LCD)
515 RF transceiver IC
640, 940 RF-ID communication section
641 RF-ID controller
642, 942 RF-ID antenna
700 IC card
941 RF-ID responder IC

The invention claimed is:

1. A puncturing device, comprising:
a puncturing mechanism including a puncturing needle configured to puncture skin, a puncturing needle holding section that holds the puncturing needle, and a biasing spring that applies a biasing force to the puncturing needle holding section, the puncturing mechanism actuating the-puncturing needle;
a puncturing mechanism control section that is configured to prevent the biasing spring from applying the biasing force to the puncturing needle holding section or to prevent the puncturing needle holding section from releasing the biasing force applied to the puncturing needle holding section;
a radio communication section that receives a radio signal from an external registration device; and
a control section that is configured to cancel the prevention of the biasing spring from applying the biasing force or the prevention of the puncturing needle holding section from releasing the biasing force when the radio communication section receives a predetermined radio signal,
wherein the puncturing mechanism includes a biasing operation section including a knob which is configured to be pulled by a user so as to apply the biasing force to the puncturing needle holding section, and
wherein the puncturing mechanism control section is configured to prevent the knob from being pulled.

2. The puncturing device according to claim 1,
wherein the radio communication section receives a puncturing allowing signal from the external registration device.

3. The puncturing device according to claim 1,
wherein the radio communication section communicates with the external registration device to transmit and receive a radio signal.

4. The puncturing device according to claim 3,
wherein the radio communication section transmits a puncturing allowing request signal to the external registration device.

5. The puncturing device according to claim 1,
wherein the radio communication section performs wireless authentication of the radio signal.

6. The puncturing device according to claim 1,
wherein the radio communication section performs radio communication by a radio frequency-identification communication scheme, a specific short-range radio communication scheme, or a low power short-range bidirectional radio communication scheme.

7. The puncturing device according to claim 1,
wherein the puncturing mechanism control section includes a puncturing execution button to be pressed by a user so as to perform puncturing with the needle, and
wherein the control section is configured to cancel the prevention of the biasing spring from applying the biasing force or the prevention of the puncturing needle holding section from releasing the biasing force when the puncturing execution button is pressed by the user.

8. A puncturing device, comprising:
a puncturing mechanism including a puncturing needle configured to puncture skin, a puncturing needle holding section that holds the puncturing needle, and a biasing spring that applies a biasing force to the puncturing needle holding section, the puncturing mechanism actuating the-puncturing needle;
a puncturing mechanism control section that is configured to prevent the biasing spring from applying the biasing force to the puncturing needle holding section or to prevent the puncturing needle holding section from releasing the biasing force applied to the puncturing needle holding section;
a radio communication section that receives a radio signal from an external registration device; and
a control section that is configured to cancel the prevention of the biasing spring from applying the biasing force or the prevention of the puncturing needle holding section from releasing the biasing force when the radio communication section receives a predetermined radio signal,
wherein the puncturing mechanism control section includes a puncturing execution button to be pressed by a user so as to perform puncturing with the needle, and
wherein the control section is configured to cancel the prevention of the biasing spring from applying the biasing force or the prevention of the puncturing needle holding section from releasing the biasing force when the puncturing execution button is pressed by the user.

9. The puncturing device according to claim 8,
wherein the radio communication section receives a puncturing allowing signal from the external registration device.

10. The puncturing device according to claim 8,
wherein the radio communication section communicates with the external registration device to transmit and receive a radio signal.

11. The puncturing device according to claim 10,
wherein the radio communication section transmits a puncturing allowing request signal to the external registration device.

12. The puncturing device according to claim 8,
wherein the radio communication section performs wireless authentication of the radio signal.

13. The puncturing device according to claim 8,
wherein the radio communication section performs radio communication by a radio frequency-identification communication scheme, a specific short-range radio communication scheme, or a low power short-range bidirectional radio communication scheme.

* * * * *